United States Patent [19]
Krebbers et al.

[11] Patent Number: 5,880,331
[45] Date of Patent: Mar. 9, 1999

[54] USE OF ANTHOCYANIN GENES TO MAINTAIN MALE STERILE PLANTS

[75] Inventors: Enno Krebbers, Houston, Tex.; Mark Williams, Gent; Jan Leemans, Deurle, both of Belgium

[73] Assignee: Plant Genetic Systems, N.V., Gent, Belgium

[21] Appl. No.: 485,139

[22] Filed: Jun. 7, 1995

Related U.S. Application Data

[63] Continuation-in-part of Ser. No. 254,776, Jun. 6, 1994, abandoned.

[51] Int. Cl.$^6$ .............................. A01H 4/00; A01H 1/00; C12N 15/05; C12N 15/00

[52] U.S. Cl. .................................. 800/205; 800/DIG. 56; 435/172.3; 435/172.1; 536/24.1; 536/27.1; 47/58; 47/DIG. 4

[58] Field of Search ................................. 536/24.1, 27.1; 800/205, 200; 435/172.3, 172.1; 47/58, DIG. 7

[56] References Cited

U.S. PATENT DOCUMENTS

| | | | |
|---|---|---|---|
| 3,842,538 | 10/1974 | Barabas | 47/58 |
| 4,727,219 | 2/1988 | Brar et al. | 435/172.3 |
| 5,356,799 | 10/1994 | Fabijanski et al. | 435/17.3 |
| 5,525,716 | 6/1996 | Olsen et al. | 538/24.1 |

FOREIGN PATENT DOCUMENTS

| | | | |
|---|---|---|---|
| 198288 | 10/1986 | European Pat. Off. | 435/172.3 |
| 344029 | 11/1989 | European Pat. Off. | 800/205 |
| 412911 | 2/1991 | European Pat. Off. | 800/205 |
| 91/02059 | 2/1991 | WIPO | 435/172.3 |
| 92/09696 | 6/1992 | WIPO | 435/172.3 |
| 93/25695 | 12/1993 | WIPO | 435/172.3 |

OTHER PUBLICATIONS

V. Chandler, et al. "Two Regulatory Genes of the Maize Anthocyanin Pathway are Homologous: Isolation of B Utilizing R Genomic Sequences", *The Plant Cell* (1989) 1:1175–1183.

E. Coe, "Anthocyanin Genetics", *The Maize Handbook* (1994) pp. 279–281.

K. Cone et al., "Maize Anthocyanin Regulatory Gene pi is a Duplicate of c1 that Functions in the Plant", *The Plant Cell* (1993) 5:1795–1805.

G. Consonni et al., "Molecular Homology Among Members of the R Gene Family in Maize", *The Plant Journal* (1993)3:335–346, No. 2.

H. Dooner et al., "Genetic and Developmental Control of Anthocyanin Biosynthesis", *Annu. Rev. Genet* (1991) 25:173–99.

W. Galinat, "Use of Male–Sterile 1 Gene to Eliminate Detasseling in Production of Hybrid Seed of Bicolor Sweet Corn", *The Journal of Heredity* (1975) 66:387–388.

S. Goff et al., "Functional Analysis of the Transcriptional Activator Encoded by the Maize B Gene: Evidence for a Direct Functional Interaction Between Two Classes of Regulatory Proteins", *Genes & Development* (1992) 6:864–875.

S. Goff et al., "Identification of Functional Domains in the Maize Transcriptional Activator C1: Comparison of Wild–Type and Dominant Inhibitor Proteins", *Genes & Development* (1991) 5:298–309.

(List continued on next page.)

*Primary Examiner*—Gary Benzion
*Attorney, Agent, or Firm*—Burns, Doane, Swecker & Mathis, LLP

[57] ABSTRACT

This invention is directed to a method to maintain male sterility in corn by the genetic linkage via genetic engineering of a homozygous male-fertility gene with a color linked restorer and plant comprising said genes. Color genes disclosed as useful in this invention include those involved in anthocyanin biosynthesis, which in corn are under the control of as many as 20 or more genes. In particular, the use of the anthocyanin color genes R, B and C1, and specific regulatory elements sequences are taught.

45 Claims, 4 Drawing Sheets

OTHER PUBLICATIONS

J. Goodrich et al., "A Common Gene Regulates Pigmentation Pattern in Diverse Plant Species", *Cell* (1992) 68:955–964.

Hartley, "Barnase and Barstar—Expression of Its Clones Inhibitor Permits Expression of a Cloned Ribonuclease", *J. Mol. Biol.* (1988) 202:913–915.

Ch. Jayaram et al., "Anthocyanin Pigmentation and Transposable Elements in Maize Aleurone", *Plant Breeding Reviews* (1990) 8:91–137.

K. Kaukis et al., "Sweet Corn Breeding", *Breeding Vegetable Crops* (1986) pp. 475–598.

T. Klein, "Regulation of Anthocyanin Biosynthetic Genes Introduced into Intact Maize Tissues by Microprojectiles", *Proc. Natl. Acad. Sci.* (1989) 86:6681–6685.

S. Ludwig, "Lc, a Member of the Maize R Gene Family Responsible for Tissue–Specific Anthocyanin Production, Encodes a Protein Similar to Transcriptional Activators and Contains a myc–homology Region", *Proc.Natl.Acad.Sci.* (1989) 86:7092–7096.

J. Paz–Ares et al. "Molecular Analysis of the C1–I allele from *Zea mays*: a Dominant Mutant of the Regulatory C1 Locus", *The EMBO Journal* (1990) 9:315–321, No. 2.

J. Paz–Ares et al., "The Regulatory c1 Locus of *Zea mays* Encodes a Protein With Homology to myb Proto–oncogene Products and with Structural Similarities to Transcriptional Activators", *The EMBO Journal* (1987) 6:3553–3558 No. 12.

G. Perrot et al. "Nucleotide Sequence of the Maize R–S Gene", *Nucleic Acids Research* (1989) 17:8003, No. 19.

F. Quattrocchio et al., "Regulatory Genes Controlling Anthocyanin Pigmentation Are Functionally Conserved Among Plant Species and Have Distinct Sets of Target Genes", *The Plant Cell* (1993) 5:1497–1512.

J. P. Radicella et al., "Cloning and Nucleotide Sequence of cDNA encoding B–Peru, a Regulatory Protein of the Anthocyanin Pathway in Maize", *Plant Molecular Biology* (1991) 17:127–130.

J.P. Radicella et al., "Allelic Diversity of the Maize B Regulatory Gene: Different Leader and Promoter Sequences of two B Alleles Determine Distinct Tissue Specificities of Anthocyanin Production", *Genes & Development* (1992) 6:2152–2164.

B. Scheffler, "Molecular Analysis of C1 Alleles in *Zea mays* Defines Regions Involved in the Expression of This Regulatory Gene", *Mol. Gen. Genet* (1994) 242:40–48.

N. Stoskopf, "Plant Breeding: Theory and Practice" Westview Press, Chapter 22, pp. 453–472, (1993).

Mariani et al., "Induction of Male Sterility in Plants by a Chimaeric Ribonuclease Gene", *Nature* (1990) 347:737–741, No. 6295.

K. Cone et al., "Cloned Anthocyanin Genes and Their Regulation", *The Maize Handbook*, M. Freeling, V. Walbot eds. Springer Verlag, New York, Inc. pp. 282–285 (1993).

G. Consonni et al. "cDNA Nucleotide Sequence of Sn, a Regulatory Gene in Maize", *Nucleic Acids Research*, (1992) 20:373 No. 2.

S. Goff et al. "Transactivation of Anthocyanin Biosynthetic Genes Following Transfer of B Regulatory Genes into Maize Tissues", *EMBO Journal* (1990) 9:2517–2522, No. 8.

Mariani et al. A chimeric ribonuclease–inhibitor gene restores fertiltiy to male sterile plants. Nature vol. 357, Jun. pp. 384–387, 1992.

Neuffer et al. "The mutants of Maize" Publication of the Crop Science Societyof America, p. 67, 1968.

Poehlman "Field Crop Breeding" AVI Publishing, pp. 473–476, 1987.

1. Transform a plant of line A with male-sterility gene S $A^{S/-}$

2. Transform a plant of line A with color-linked restorer gene Rf: $A^{Rf/-}$

3. Cross the plants of 1 and 2
   Progeny Table of $A^{S/-} \times A^{Rf/-}$

| | S,— | —,Rf | —,— |
|---|---|---|---|
| | | $A^{S/-}, R^{f/-}$ | $A^{S/-}, -/-$ |
| | | $A^{-/-}, R^{f/-}$ | $A^{-/-}, -/-$ |

4. Select the progeny from the cross of 3 with both the S and Rf genes (e.g. by means of PCR, or by presence of linked selectable marker genes)

5. Cross the $A^{S/-}, R^{f/-}$ plants from 4 with $A^{S/-}$ progeny Table of $A^{S/-}, R^{f/-} \times A^{S/-, -/-}$

| | S, Rf | S,— | —,Rf | —,— |
|---|---|---|---|---|
| | $A, S/S, Rf/-$ | $A^{S}/S,-/-$ | $A^{S/-}, Rf/-$ | $A^{S/-}, -/-$ |
| | $A^{S/-}, Rf/-$ | $A^{S/-}, -/-$ | $A^{-/-}, Rf/-$ | $A^{-/-}, -/-$ |

FIG. IA

6. Select colored seeds, grow into plants and self all plants that contain both the S and Rf genes (e.g. by means of PCR, or by presence of linked selectable marker genes)

Two possible progeny tables depending on the genotype of the selfed plant.

| Genotype of selfed plant | Frequency of progeny | Frequency of genotype in progeny | Color phenotype of progeny seeds | Male-Fertility phenotype of progeny plants |
|---|---|---|---|---|
| S/–,Rf/– | Genotypes as in progency table in 5 | 75% | colored seeds | fertile |
|  |  | 25% | non-colored seeds | 75% fertile, 25% sterile |
| S/S, Rf/– |  | 25% | colored seeds | fertile |
|  |  | 50% | colored seeds | fertile |
|  |  | 25% | non-colored seeds | sterile |
| S/S, –/– |  |  |  |  |

Progeny which display 75% colored and 25% non-colored seeds and in which all non-colored seeds grow into male-sterile plants are retained.

FIG. IB

7. Cross the male-sterile plants of the retained progeny of 6 with the male-fertile plants of the retained progeny in 6.
Analyze progeny of each cross. Two types of crosses are possible:
1) S/S, Rf/Rf × S/S,–/–, or
2) S/S,Rf/– × S/S,–/–

| Cross | Genotype of progeny | Frequency of genotype in progeny | Color phenotype of progeny seeds | Male-Fertility phenotype of progeny plants |
|---|---|---|---|---|
| S/S,Rf/Rf × S/S,–/– | S/S,Rf/– | 100% | colored seeds | fertile |
| S/S,Rf/– × S/S,–/– | S/S,Rf/– | 50% | colored seeds | fertile |
|  | S/S,–/– | 50% | non-colored seeds | sterile |

The progeny of the cross which produce 50% colored seeds and 50% non-colored seeds are retained. The non-colored seeds will all grow into male-sterile first parent plants of this invention, while the colored seeds will all grow into male-fertile second parent plants of this invention.

8. Maintain first and second parent plants by crossing the first and second parent plants and harvesting of the progeny from the male-sterile first parent plant.

Progeny Table of A S/S,–/– × AS/S,Rf/–

|  | S,Rf | S,– |
|---|---|---|
| S,– | A S/S,Rf/– | A S/S,–/– |

Seeds which will grow into sterile and fertile plants can be separated on the basis of seed color.

FIG. 1C

USE OF ANTHOCYANIN GENES TO MAINTAIN MALE STERILE PLANTS

CROSS REFERENCE TO RELATED APPLICATIONS

This application is a continuation-in-part of application Ser. No. 08/254,776, filed on Jun. 6, 1994, now abandoned.

The present invention relates to a method to maintain male-sterile plants that can be used for the production of hybrid seed of a plant crop species, to transgenic inbred plants that can be used in such process, and to chimeric genes that can be used to produce such transgenic inbred plants.

BACKGROUND OF THE INVENTION

In many, if not most plant species, the development of hybrid cultivars is highly desired because of their generally increased productivity due to heterosis: the superiority of performance of hybrid individuals compared with their parents (see e.g., Fehr, 1987, Principles of cultivar development, Vol. 1: Theory and Technique, MacMillan Publishing Co., New York; Allard, 1960, Principles of Plant Breeding, John Wiley and Sons, Inc.).

The development of hybrid cultivars of various plant species depends upon the capability of achieving essentially almost complete cross-pollination between parents. This is most simply achieved by rendering one of the parent lines male sterile (i.e. bringing them in a condition so that pollen is absent or nonfunctional) either manually, by removing the anthers, or genetically by using, in the one parent, cytoplasmic or nuclear genes that prevent anther and/or pollen development (for a review of the genetics of male sterility in plants see Kaul, 1988, 'Male Sterility in Higher Plants', Springer Verlag).

For hybrid plants where the seed is the harvested product (e.g. corn, oilseed rape) it is in most cases also necessary to ensure that fertility of the hybrid plants is fully restored. In systems in which the male sterility is under genetic control this requires the existence and use of genes that can restore male fertility. The development of hybrid cultivars is mainly dependent on the availability of suitable and effective sterility and restorer genes.

Endogenous nuclear loci are known for most plant species that may contain genotypes which effect male sterility, and generally, such loci need to be homozygous for particular recessive alleles in order to result in a male-sterile phenotype. The presence of a dominant 'male fertile' allele at such loci results in male fertility.

Recently it has been shown that male sterility can be induced in a plant by providing the genome of the plant with a chimeric male-sterility gene comprising a DNA sequence (or male-sterility DNA) coding, for example, for a cytotoxic product (such as an RNase) and under the control of a promoter which is predominantly active in selected tissue of the male reproductive organs. In this regard stamen-specific promoters, such as the promoter of the TA29 gene of *Nicotiana tabacum*, have been shown to be particularly useful for this purpose (Mariani et al., 1990, Nature 347:737, European patent publication ("EP") 0,344,029). By providing the nuclear genome of the plant with such a male-sterility gene, an artificial male-sterility locus is created containing the artificial male-sterility genotype that results in a male-sterile plant.

In addition it has been shown that male fertility can be restored to the plant with a chimeric fertility-restorer gene comprising another DNA sequence (or fertility-restorer DNA) that codes, for example, for a protein that inhibits the activity of the cytotoxic product or otherwise prevents the cytotoxic product from being active in the plant cells (European patent publication "EP" 0,412,911). For example the barnase gene of *Bacillus amyloliquefaciens* codes for an RNase, called barnase, which can be inhibited by a protein, barstar, that is encoded by the barstar gene of *B. amylolicruefaciens*. The barnase gene can be used for the construction of a sterility gene while the barstar gene can be used for the construction of a fertility-restorer gene. Experiments in different plant species, e.g. oilseed rape, have shown that a chimeric barstar gene can fully restore the male fertility of male sterile lines in which the male sterility was due to the presence of a chimeric barnase gene (EP 0,412,911, Mariani et al., 1991, Proceedings of the CCIRC Rapeseed Congress, Jul. 9–11, 1991, Saskatoon, Saskatchewan, Canada; Mariani et al., 1992, Nature 357:384). By coupling a marker gene, such as a dominant herbicide resistance gene (for example the bar gene coding for phosphinothricin acetyl transferase (PAT) that converts the herbicidal phosphinothricin to a non-toxic compound [De Block et al., 1987, EMBO J. 6:2513]), to the chimeric male-sterility and/or fertility-restorer gene, breeding systems can be implemented to select for uniform populations of male sterile plants (EP 0,344,029; EP 0,412,911).

The production of hybrid seed of any particular cultivar of a plant species requires the: 1) maintenance of small quantities of pure seed of each inbred parent, and 2) the preparation of larger quantities of seed of each inbred parent. Such larger quantities of seed would normally be obtained by several (usually two) seed multiplication rounds, starting from a small quantity of pure seed ("basic seed") and leading, in each multiplication round, to a larger quantity of pure seed of the inbred parent and then finally to a stock of seed of the inbred parent (the "parent seed" or "foundation seed") which is of sufficient quantity to be planted to produce the desired quantities of hybrid seed. Of course, in each seed multiplication round larger planting areas (fields) are required.

In order to maintain and enlarge a small stock of seeds that can give rise to male-sterile plants it is necessary to cross the male sterile plants with normal pollen-producing parent plants. In the case in which the male-sterility is encoded in the nuclear genome, the offspring of such cross will in all cases be a mixture of male-sterile and male-fertile plants and the latter have to be removed from the former. With male-sterile plants containing an artificial male-sterility locus as described above, such removal can be facilitated by genetically linking the chimeric male sterility gene to a suitable marker gene, such as the bar gene, which allows the easy identification and removal of male-fertile plants (e.g. by spraying of an appropriate herbicide).

However, even when suitable marker genes are linked to male-sterility genotypes, the maintenance of parent male-sterile plants still requires at each generation the removal from the field of a substantial number of plants. For instance in systems using a herbicide resistance gene (e.g. the bar gene) linked to a chimeric male-sterility gene, as outlined above, only half of the parent stock will result in male-sterile plants, thus requiring the removal of the male-fertile plants by herbicide spraying prior to flowering. In any given field, the removal of male-fertile plants effectively reduces the potential yield of hybrid seed or the potential yield of male-sterile plants during each round of seed multiplication for producing parent seed. In addition removal of the male-fertile plants may lead to irregular stands of the male-sterile plants. For these reasons removal of the male-fertile plants is economically unattractive for many important crop species such as corn and oilseed rape.

Anthocyanins are pigments that are responsible for many of the red and blue colors in plants. The genetic basis of anthocyanin biosynthesis has been well characterized, particularly in corn, Petunia, and Antirrhinium (Dooner et al, 1991, Ann.Rev.Genet. 25:179–199; Jayaram and Peterson, 1990, Plant Breeding Reviews 2:91–137; Coe, 1994, In 'The Maize Handbook', Freeling and Walbot, eds. Springer Verlag New York Inc., p. 279–281). In corn anthocyanin biosynthesis is apparently under control of 20 or more genes. The structural loci C2, Whp, A1, A2, Bz1, and Bz2 code for various enzymes involved in anthocyanin biosynthesis and at least 6 regulatory loci, acting upon the structural genes, have been identified in corn i.e. the R, B, C1, Pl, P and Vp1 loci.

The R locus has turned out to be a gene family (in corn located on chromosome 10) comprising at least three different genes i.e. R (which itself may comprise duplicate genes organized in a tandem array), and the displaced duplicate genes R(Sn) and R(Lc). R typically conditions pigmentation of the aleurone but various alleles are known to confer distinct patterns of pigmentation. R(Lc) is associated with unique pigmentation of leaves and R(Sn) with unique pigmentation of the scutellar node. One state of R is associated with pigmentation of the whole plant (R(P)), while another is associated with pigmentation of the seeds (R(S)).

Alleles of the unlinked B locus (in corn located on chromosome 2) rarely condition pigmentation of the aleurone, but are frequently associated with pigmentation of mature plant parts. The B-peru allele however, pigments the aleurone (like R(S)). Analysis at the molecular level has confirmed that the R and B loci are duplicate genes.

In order that the R and B loci can color a particular tissue, the appropriate allele of C1 or Pl loci also needs to be present. The C1 and C1-S alleles, for instance, pigment the aleurone when combined with the suitable R or B allele.

Alleles of the C1 locus have been cloned and sequenced. of particular interest are C1 (Paz-Ares et al, 1987, EMBO J. 6:3553–3558) and C1-S (Schleffer et al, 1994, Mol.Gen-.Genet. 242:40–48). Analysis of the sequences revealed the presence of two introns in the coding region of the gene. The protein encoded by the C1 and C1-S alleles shares homology with mvb proto-oncogenes and is known to be a nuclear protein with DNA-binding capacity acting as transcriptional activators.

The cDNA of the B-peru allele has also been analyzed and sequenced (Radicella et al, 1991, Plant Mol. Biol. 17:127–130). Genomic sequences of B-peru were also isolated and characterized based on the homology between R and B (Chandler et al., 1989, the Plant Cell 1:1175–1183; Radicella et al., 1992, Genes & Development 6:2152–2164). The tissue specificity of anthocyanin production of two different B alleles was shown to be due to differences in the promoter and untranslated leader sequences (Radicella et al, 1992, supra).

Various alleles of the R gene family have also been characterized at the molecular level, e.g. Lc (Ludwig et al, 1989, PNAS 86:7092–7096), R-nj, responsible for pigmentation of the crown of the kernel (Dellaporta et al, 1988, In "Chromosome Structure and Function,: Impact of New Concepts, 18th Stadeler Genetics Symposium, Gustafson and Appels, eds. (New York, Plenum press, pp. 263–282)), Sn (Consonni ei al, 1992, Nucl. Acids. Res. 20:373), and R(S) (Perrot and Cone, 1989, Nucl. Acids. Res. 17:8003).

The proteins encoded by the B and R genes share homology with mVc proto-oncogenes and have characteristics of transcriptional activators.

It has been shown that various structural and regulatory genes introduced in maize tissues by microprojectiles operate in a manner similar to the endogenous loci and can complement genotypes which are deficient in the introduced genes (Klein et al., 1989, PNAS 86:6681–6685; Goff et al., 1990, EMBO J. 9:2517–2522). The Lc gene was also used as a visible marker for plant transformation (Ludwig et al., 1990, Science 247:449–450). Apart from the above other genes involved in anthocyanin biosynthesis have been cloned (Cone, 1994, In 'The Maize Handbook', Freeling and Walbot eds., Springer Verlag New York Inc., p. 282–285).

In Barley, Falk et al (1981, In Barley Genetics IV, proceedings of the 4th International Barley Genetics symposium, Edinburgh University press, Edinburgh, pp. 778–785) have reported the coupling of a male-sterile gene to a xenia-expressing shrunken endosperm gene which makes it possible to select seeds, before planting, that will produce male-sterile plants. Problems associated with such proposal include complete linkage of the two genes (Stoskopf, 1993, Plant Breeding : Theory and Practice, Westview Press, Boulder, San Francisco, Oxford). In sweetcorn, a genetic system to produce hybrid corn seeds without detassling, which utilizes the closely linked genes y (white endosperm) and ms (male sterility) was suggested but was never used because of contamination from 5% recombination. Galinat (1975, J. Hered. 66:387–388) described a two-step seed production scheme that resolved this problem by using electronic color sorters to separate yellow from white kernels. This approach has not been utilized commercially (Kankis and Davis, 1986, in <<Breeding Vegetable Crops>>, the Avi Publishing Company Inc. Westport, Conn., U.S.A., p. 498).

EP 0,198,288 and U.S. Pat. No. 4,717,219 describe methods for linking marker genes (which can be visible markers or dominant conditional markers) to endogenous nuclear loci containing nuclear male-sterility genotypes.

EP 412,911 describes foreign restorer genes (e.g. barstar coding region under control of a stamen-specific promoter) that are linked to marker genes, including herbicide resistance genes and genes coding for pigments (e.g. the A1 gene) under control of a promoter which directs expression in specific cells, such as petal cells, leaf cells or seed cells, preferably in the outer layer of the seed.

SUMMARY OF THE INVENTION

The invention concerns a maintainer plant consisting essentially of cells which comprise in their genome:

a homozygous male-sterility genotype at a first genetic locus; and a color-linked restorer genotype at a second genetic locus, which is heterozygous (Rf/-) for a foreign DNA Rf comprising:

a) a fertility-restorer gene capable of preventing the phenotypic expression of said male-sterility genotype, and b) at least one anthocyanin regulatory gene involved in the regulation of anthocyanin biosynthesis in cells of seeds of said plant and which is capable of producing anthocyanin at least in the seeds of said plant, so that anthocyanin production in the seeds is visible externally.

The invention also concerns an anthocyanin regulatory gene which is a shortened R, B or C1 gene or a combination of shortened R, B or C1 genes which is functional for conditioning and regulating anthocyanin production in the aleurone.

The invention also includes a DNA such as a plasmid comprising a fertility-restorer gene capable of preventing the phenotypic expression of a male-sterility genotype in a plant and at least one anthocyanin regulatory gene involved in the regulation of anthocyanin biosynthesis in cells of seeds of a plant and which is capable of producing anthocyanin at least in the seeds of a plant, so that anthocyanin production in the seeds is visible externally.

Also within the scope of the invention is a process to maintain a line of male-sterile plants, which comprises the following steps:

i) crossing:
   a) a male-sterile parent plant of said line having, in a first genetic locus, a homozygous male-sterility genotype, and
   b) a maintainer parent plant of said line consisting essentially of cells which comprise, stably intergrated in their nuclear genome:
       a homozygous male-sterility genotype at a first genetic locus; and
       a colored-linked restorer genotype at a second genetic locus, which is heterozygous for a foreign DNA comprising:
         i) a fertility-restorer gene capable of preventing the phenotypic expression of said male-sterility genotype, and
         ii) at least one anthocyanin regulatory gene involved in the regulation of anthocyanin biosynthesis in cells of seeds of said plant which is capable of producing anthocyanin at least in the seeds of said plant, so that anthocyanin production in the seeds is visible externally,
ii) obtaining the seeds from said parent plants, and
iii) separating on the basis of color, the seeds in which no anthocyanin is produced and which grow into male-sterile parent plants.

Preferably, the genome of the male-sterile parent plant does not contain at least one anthocyanin regulatory gene necessary for the regulation of anthocyanin biosynthesis in seeds of this plant to produce externally visible anthocyanin in the seeds. In one embodiment of the invention, the genome of the male-sterile parent plant contains a first anthocyanin regulatory gene and the genome of the maintainer plant a second anthocyanin regulatory gene which, when present with the first anthocyanin regulatory gene in the genome of a plant, is capable of conditioning the production of externally visible anthocyanin in seeds.

The invention also concerns a process to maintain a line of maintainer plants, which comprises the following steps:
i) crossing:
   a) a male-sterile parent plant as described previously, and
   b) a maintainer parent plant as described previously,
ii) obtaining the seeds from said male-sterile parent plant, and
iii) separating on the basis of color, the seeds in which anthocyanin is produced and which grow into maintainer parent plants.

The invention also relates to a kit for maintaining a line of male-sterile or maintainer plants, said kit comprising:
a) a male-sterile parent plant of said line as described previously, having, in a first genetic locus, a homozygous male-sterility genotype and which is incapable of producing externally visible anthocyanin in seeds, and
b) a maintainer parent plant of said line as described previously.

Also within the scope of the invention is a process to maintain the kit described previously which comprises:
crossing said male-sterile parent plant with said maintainer parent plant;
obtaining the seeds from said male-sterile parent plants and optionally the seeds from said maintainer parent plant in which no anthocyanin is produced; and
optionally growing said seeds into male-sterile parent plants and maintainer parent plants.

As mentioned above, the present invention provides means to maintain a line of male-sterile plants, particularly corn or wheat plants. These means can be in the form of a process which comprises the following steps:
i) crossing A) a first parent plant of said line, which is male-sterile, and which is genetically characterized by the absence of at least one anthocyanin regulatory gene thereby being incapable of producing anthocyanin in seeds, particularly in the aleurone layer, and also by having at a first genetic locus a homozygous male-sterility genotype, and B) a second parent plant of said line, which is male-fertile, and which is genetically characterized by having at said first genetic locus, said homozygous male-sterility genotype, and at a separate second genetic locus the genotype Rf/-,
whereby,
Rf is a foreign chimeric DNA (the "color-linked restorer gene") stably integrated in the nuclear genome of said plant which comprises:
   a) a fertility-restorer gene that is capable of preventing the phenotypic expression, i.e. the male-sterility, of said male-sterility genotype.
   b) said at least one anthocyanin regulatory gene (the "color gene") involved in the regulation of the anthocyanin biosynthesis in cells of seeds of said cereal plant which is capable of producing anthocyanin at least in the seeds, particularly in the aleurone, of said cereal plant,
ii) obtaining the seeds from said first parent plants
iii) separating, on the basis of color, the seeds in which no anthocyanin is produced and in which the genotype at said first genetic locus is said homozygous male-sterility genotype and the genotype at said second genetic locus is -/-, and the seeds in which anthocyanin is produced and in which the genotype at said first genetic locus is said homozygous male-sterility genotype and the genotype at said second genetic locus is Rf/-.

Of particular interest in the invention is a second parent plant in which said at least one anthocyanin regulatory gene comprises a gene derived from a genomic clone of an R or B gene, particularly an R or B gene that conditions anthocyanin production in the aleurone, preferably the B-peru allele (e.g. the shortened B-peru gene in pCOL13), and/or comprises a gene derived from a genomic clone of the C1 gene (e.g. the gene with the sequence of SEQ ID NO 1 or SEQ ID NO 5) or the C1-S gene.

The first genetic locus can be endogenous to plants of said line (in which case the homozygous male-sterility genotype will be m/m), but is preferably a foreign locus with genotype S/S in which S is a foreign DNA which, when expressed in a plant is capable of rendering the plant male-sterile. A preferred foreign DNA comprises at least:
s1) a male-sterility DNA encoding a RNA, protein or polypeptide which, when produced or overproduced in a cell of the plant, significantly disturbs the metabolism, functioning and/or development of the cell, and,
s2) a sterility promoter capable of directing expression of the male-sterility DNA selectively in stamen cells, preferably tapetum cells, of the plant; the male-sterility DNA being in the same transcriptional unit as, and under the control of, the sterility promoter.

In case such a foreign male-sterility genotype is used, the fertility-restorer gene in the foreign DNA Rf preferably comprises at least:

a1) a fertility-restorer DNA encoding a restorer RNA, protein or polypeptide which, when produced or overproduced in the same stamen cells as said male-sterility gene S, prevents the phenotypic expression of said foreign male-sterility genotype comprising S, and, a2) a restorer promoter capable of directing expression of the fertility-restorer DNA at least in the same stamen cells in which said male-sterility gene S is expressed, so that the phenotypic expression of said male-sterility gene is prevented; the fertility-restorer DNA being in the same transcriptional unit as, and under the control of, the restorer promoter.

In case of an endogenous male-sterility genotype which is homozygous for the recessive male-sterility allele m, the fertility restorer gene is preferably a DNA comprising the dominant allele M of said locus.

The present invention also provides the novel foreign chimeric DNA Rf as used in the second parent plants, plasmids comprising these chimeric genes, and host cells comprising these plasmids.

The present invention also provides the shortened B-peru gene in pCOL13 (SEQ ID NO 6) and the shortened C1 gene, particularly the EcoRI-SfiI fragment of pCOL9 of SEQ ID NO 5.

The present invention further provides plants the nuclear genome of which is transformed with the foreign chimeric DNA Rf, particularly the second parent plant.

BRIEF DESCRIPTION OF THE DRAWINGS

FIG. 1 depicts a breeding scheme for obtaining the first and second parent plants according to the invention.

DETAILED DESCRIPTION OF THE INVENTION

Figure 2:
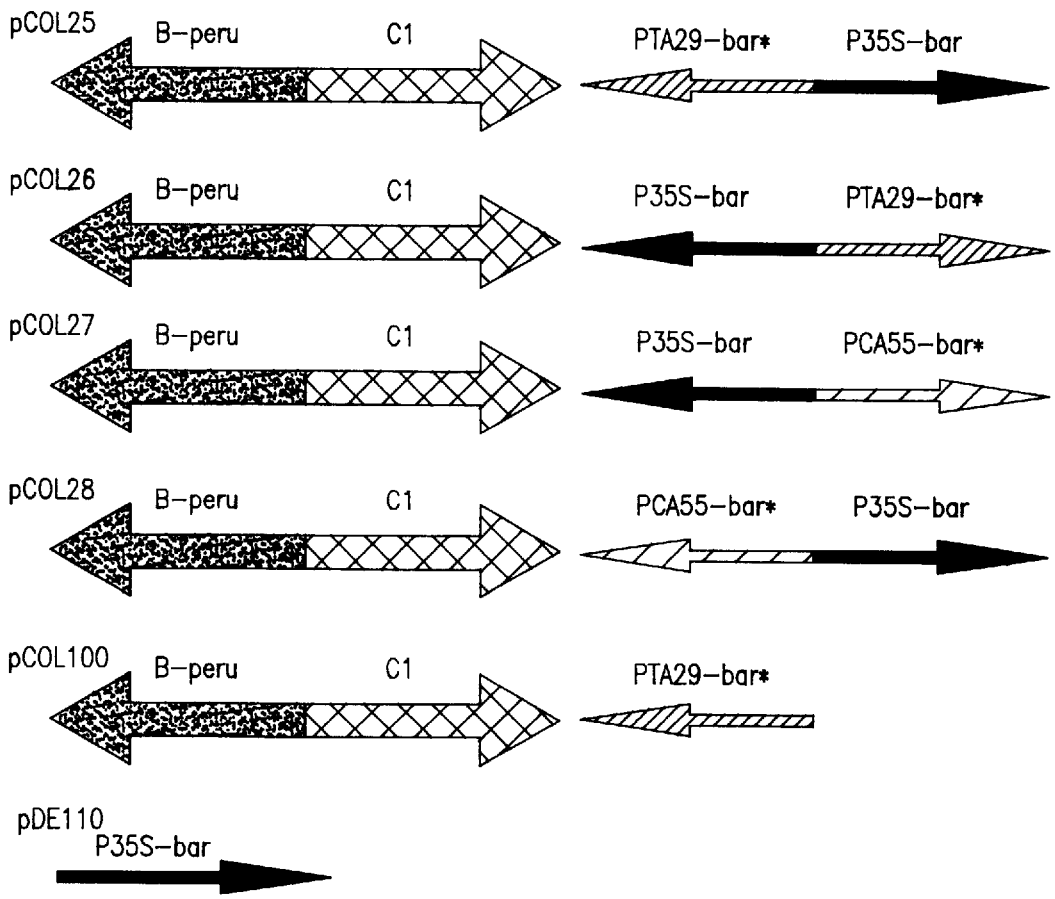
FIG. 2 depicts the schematic structure of pCOL25, pCOL26, pCOL27, pCOL28, pCOL100 and pDE110.

A male-sterile plant is a plant of a given plant species which is male-sterile due to expression of a male-sterility genotype such as a foreign male-sterility genotype containing a male-sterility gene. A restorer plant is a plant of the same plant species that contains within its genome at least one fertility-restorer gene that is able to restore the male fertility in those offspring obtained from a cross between a male-sterile plant and a restorer plant and containing both a male-sterility genotype and a fertility-restorer gene. A restored plant is a plant of the same species that is male-fertile and that contains within its genome a male-sterility genotype and a fertility-restorer gene.

A line is the progeny of a given individual plant.

A gene as used herein is generally understood to comprise at least one coding region coding for an RNA, protein or polypeptide which is operably linked to suitable promoter and 3' regulatory sequences. A structural gene is a gene whose product is a e.g. an enzyme, a structural protein, tRNA or rRNA. For example anthocyanin structural genes encode-enzymes (e.g. chalcone synthase) directly involved in the biosynthesis of anthocyanins in plant cells. A regulatory gene is a gene which encodes a regulator protein which regulates the transcription of one or more structural genes. For example the R, B, and C1 genes are regulatory genes that regulate transcription of anthocyanin structural genes.

For the purpose of this invention the expression of a gene, such as a chimeric gene, will mean that the promoter of the gene directs transcription of a DNA into a mRNA which is biologically active i.e. which is either capable of interacting with another RNA, or which is capable of being translated into a biologically active polypeptide or protein.

The phenotype is the external appearance of the expression (or lack of expression) of a genotype i.e. of a gene or set of genes (e.g. male-sterility, seed color, presence of protein or RNA in specific plant tissues etc.)

As used herein, a genetic locus is the position of a given gene in the nuclear genome, i.e. in a particular chromosome, of a plant. Two loci can be on different chromosomes and will segregate independently. Two loci can be located on the same chromosome and are then generally considered as being linked (unless sufficient recombination can occur between them).

An endogenous locus is a locus which is naturally present in a plant. A foreign locus is a locus which is formed in the plant because of the introduction, by means of genetic transformation, of a foreign DNA.

In diploid plants, as in any other diploid organisms, two copies of a gene are present at any autosomal locus. Any gene can be present in the nuclear genome in several variant states designated as alleles. If two identical alleles are present at a locus that locus is designated as being homozygous, if different alleles are present, the locus is designated as being heterozygous. The allelic composition of a locus, or a set of loci, is the genotype. Any allele at a locus is generally represented by a separate symbol (e.g. M and m, S and -, - representing the absence of the gene). A foreign locus is generally characterized by the presence and/or absence of a foreign DNA. A heterozygous genotype in which one allele corresponds to the absence of the foreign DNA is also designated as hemizygous (e.g. Rf/-). A dominant allele is generally represented by a capital letter and is usually associated with the presence of a biologically active gene product (e.g. a protein) and an observable phenotypic effect (e.g. R indicates the production of an active regulator protein and under appropriate conditions anthocyanin production in a given tissue while r indicates that no active regulator protein is produced possibly leading to absence of anthocyanin production).

A plant can be genetically characterized by identification of the allelic state of at least one genetic locus.

The genotype of any given locus can be designated by the symbols for the two alleles that are present at the locus (e.g. M/m or m/m or S/-). The genotype of two unlinked loci can be represented as a sequence of the genotype of each locus (e.g. S/S,Rf/-)

The nuclear male-sterility genotype as used in this invention refers to the genotype of at least one locus, preferably only one locus, in the nuclear genome of a plant (the "male-sterility locus") the allelic composition of which may result in male sterility in the plant. A male-sterility locus may be endogenous to the plant, but it is generally preferred that it is foreign to the plant.

Foreign male-sterility loci are those in which the allele responsible for male sterility is a foreign DNA sequence S (the "male-sterility gene") which when expressed in cells of the plant make the plant male-sterile without otherwise substantially affecting the growth and development of the plant. Such male-sterility gene preferably comprises at least:

s1) a male-sterility DNA encoding a sterility RNA, protein or polypeptide which, when produced or overproduced in a stamen cell of the plant, significantly disturbs the metabolism, functioning and/or development of the stamen cell, and, s2) a sterility promoter capable of directing expression of the male-sterility DNA selectively in stamen cells (e.g. anther cells or tapetum cells) of the plant; the male-sterility DNA being in the same transcriptional unit as, and under the control of, the sterility promoter.

The male-sterility locus preferably also comprises in the same genetic locus at least one first marker gene T which comprises at least:

t1) a first marker DNA encoding a first marker RNA, protein or polypeptide which, when present at least in a specific tissue or specific cells of the plant, renders the plant easily separable from other plants which do not contain the first marker RNA, protein or polypeptide encoded by the first marker DNA at least in the specific tissue or specific cells, and, t2) a first marker promoter capable of directing expression of the first marker DNA at least in the specific tissue or specific cells: the first marker DNA being in the same transcriptional unit as, and under the control of, the first marker promoter.

Such male-sterility gene is always a dominant allele at such a foreign male-sterility locus. The recessive allele corresponds to the absence of the male-sterility gene in the nuclear genome of the plant.

Male-sterility DNAs and sterility promoters that can be used in the male-sterility genes in the first parent line of this invention have been described before (EP 0,344,029 and EP 0,412,911). For the purpose of this invention the expression of the male-sterility gene in a plant cell should be able to be inhibited or repressed for instance by means of expression of a suitable fertility-restorer gene in the same plant cell. In this regard a particular useful male-sterility DNA codes for barnase (Hartley, J.Mol. Biol. 1988 202:913). The sterility promoter can be any promoter but it should at least be active in stamen cells, particularly tapetum cells. Particularly useful sterility promoters are promoters that are selectively active in stamen cells, such as the tapetum-specific promoters of the TA29 gene of *Nicotiana tabacum* (EP 0,344,029) which can be used in tobacco, oilseed rape, lettuce, cichory, corn, rice, wheat and other plant species; the PT72, the PT42 and PE1 promoters from rice which can be used in rice, corn, wheat, and other plant species (WO 92/13956) ; the PCA55 promoter from corn which can be used in corn, rice, wheat and other plant species (WO 92/13957); and the A9 promoter of a tapetum-specific gene of *Arabidopsis thaliana* (Wyatt et al., 1992, Plant Mol. Biol. 19:611–922). However, the sterility promoter may also direct expression of the sterility DNA in cells outside the stamen; particularly if the effect of expression of the male-sterility DNA is such that it will specifically disturb the metabolism, functioning and/or development of stamen cells so that no viable pollen is produced. One example of such a male-sterility DNA is the DNA coding for an antisense RNA which is complementary to the mRNA of the chalcone synthase gene (van der Meer et al (1992) The Plant Cell 4:253–262). In this respect a useful promoter is the 35S promoter (see EP 0,344,029), particularly a 35S promoter that is modified to have enhanced activity in tapetum cells as described by van der Meer et al (1992) The Plant Cell 4:253–262 (the "35S-tap promoter").

A preferred endogenous male-sterility locus is one in which a recessive allele (hereinafter designated as m) in homozygous condition (m/m) results in male sterility. At such loci male fertility is encoded by a corresponding dominant allele (M). In many plant species such endogenous male-sterility loci are known (see Kaul, 1988, supra (in corn see also recent issues of Maize Genetics Cooperation Newsletter, published by Department of Agronomy and U.S. Department of Agriculture, University Of Missouri, Columbia, Mo., U.S.A.). The DNA sequences in the nuclear genome of the plant corresponding to m and M alleles can be identified by gene tagging i.e. by insertional mutagenesis using transposons, or by means of T-DNA integration (see e.g. Wienand and Saedler, 1987, In 'Plant DNA Infectious Agents', Ed. by T. H. Hohn and J. Schell, Springer Verlag Wien New York, p. 205; Shepherd, 1988, In 'Plant Molecular Biology: a Practical Approach', IRL Press, p. 187; Teeri et al., 1986, EMBO J. 5:1755). It will be evident that in the first and second parent plant of this invention S/S can be replaced by m/m without affecting the outcome of the process. Indeed, one feature of the process of this invention is that the male-sterility locus is homozygous thus allowing the use of 'recessive' male-sterility alleles.

Fertility-restorer DNAs that can be used in the fertility restorer gene in the second parent line of this invention have been described before (EP 0,412,911).

In this regard, fertility-restorer genes in which the fertility-restorer DNA encodes barstar (Hartley, J.Mol. Biol. 1988 202:913) are particularly useful to inhibit the expression of a male-sterility DNA that encodes barnase. In this regard it is believed that a fertility-restorer DNA that codes for a mutant of the barstar protein, i.e. one in which the Cysteine residue at position 40 in the protein is replaced by serine (Hartley, 1989, TIBS 14:450), functions better in restoring the fertility in the restored plants of some species.

In principle any promoter can be used as a restorer promoter in the fertility restorer gene in the second parent line of this invention. The only prerequisite is that such second parent plant, which contains both the color gene and the fertility-restorer gene, should be phenotypically normal and male-fertile. This requires that the restorer promoter in the fertility-restorer gene should be at least active in those cells of a plant of the same species in which the sterility promoter of the corresponding male-sterility gene can direct expression of the male-sterility DNA. In this regard it will be preferred that the sterility promoter and the restorer promoter are the same; they can for example be both stamen-specific promoters (e.g. the TA29 promoter or the CA55 promoter) or they can be both constitutive promoters (such as the 35S or 35S-tap promoter). However, the sterility promoter may be active only in stamen cells while the restorer promoter is also active in other cells. For instance, the sterility promoter can be a stamen-specific (such as the TA29 or CA55 promoter) while the restorer promoter is the 35S-tap promoter.

When the male sterility to be restored is due to the male-sterility genotype at an endogenous male-sterility locus being homozygous for a recessive allele m, it is preferred that the fertility-restorer gene is the dominant allele of that male-sterility locus, preferably under control of its own promoter. The DNA corresponding to such a dominant allele, including its natural promoter can be isolated from the nuclear genome of the plant by means of gene tagging as described above.

The nature of the color gene that is used in the color-linked restorer gene in the second parent plant of this invention depends upon the genotype of the untransformed plants of the same line. Preferably, only cereal plants with a genotype that does not condition externally visible anthocyanin production in seeds, particularly in the aleurone can be used to produce the second parent plants. These plants usually have a genotype in which no functional copy of a suitable regulatory gene such as the R or B gene, and/or the C1 gene, is present.

In corn, for instance, all of the currently used inbred lines in the U.S.A. are r-r (pink anthers, leaf tips, plant base) or r-g (green) and most of these are c1 and pl; at the B- locus the B-peru allele is very rare (Coe et al, 1988, In 'Corn and Corn Improvement', 3rd edition, G. F. Sprague and J. W. Dudley, eds. America Science of Agronomy, Inc. Publishers, Madison, Wis., U.S.A.). The result is that no anthocyanins are produced in the aleurone of these lines and that the kernels are yellow. This requires that when these lines are transformed with a color-linked restorer gene, the color gene should consist of a functional R or B gene which conditions anthocyanin production in aleurone, and usually also a functional C1 gene capable of conditioning anthocyanin production in aleurone.

A useful R or B gene is the B-peru gene, but of course also other R genes could be used such as the R(S) gene (Perrot and Cone, 1989, Nucl. Acids Res. 17:8003). In this regard a gene derived from genomic clones of the B-peru gene (Chandler et al, 1989, The Plant Cell 1:1175–1183) is believed to be particularly useful. However the length of this genomic DNA (11 kbp) renders its practical manipulation and use for transformation by direct gene transfer, difficult, certainly in combination with other genes such as the restorer gene and the C1 gene.

In one inventive aspect of this invention it was found that the B-peru gene could be considerably shortened while still retaining, under appropriate conditions, its capability of conditioning anthocyanin production in the aleurone of seeds of cereal plants such as corn. A preferred shortened B-peru gene is that of Example 2.2 and which is contained in plasmid pCOL13 (deposited under accession number LMBP 3041).

A useful C1 gene is the genomic clone as described by Paz-Ares et al, 1987, EMBO J. 6:3553–3558. However the length of this genomic DNA (4 kbp) precludes its practical manipulation and use for transformation by direct gene transfer, certainly in combination with other genes such as the restorer gene and the B-peru gene. Nevertheless other variants of the C1 gene can also be used. In this regard Scheffler et al, 1994, Mol.Gen.Genet. 242:40–48 have described the C1-S allele which differs from the C1 allele of Paz-Ares et al, supra by a few nucleotides in the promoter region near the CAAT box and which is dominant to the wild-type allele (C1) and shows enhanced pigmentation. The C1-S gene can be easily used in this invention by appropriate changes in the C1 gene. For example the TGCAG at positions 935 to 939 in SEQ ID NO 1 (respectively at positions 884–888 in SEQ ID NO 5) can be easily changed to TTAGG yielding a C1-S allele (respectively pCOL9S).

In one inventive aspect of this invention it was found that the C1 gene (and the C1-S gene) could be considerably shortened while still retaining, under appropriate conditions, its capability of conditioning anthocyanin production in the aleurone of seeds of cereal plants such as corn. Preferred shortened C1 genes for instance are those of Example 2.1 such as comprised in pCOL9 which has the sequence of SEQ ID NO 5, particularly as comprised between the EcoRI and SfiI sites of pCOL9, and the corresponding shortened C1-S gene in pCOL9S.

The transcribed region of the shortened B-peru and C1 genes still contain some small introns which can also be deleted without affecting the function of the genes. It is also believed that the shortened B-peru and C1 genes can be somewhat further truncated at their 5' and 3' ends, without affecting their expression in aleurone. In particular it is believed that the sequence between positions 1 and 3272 of SEQ ID NO 6 can also be used as a suitable B-peru gene. It is also believed that this gene can still be truncated at its 3' end down to a position between nucleotides 2940 and 3000 of SEQ ID No. 6.

Athough the use of genomic sequences of the B-peru gene and the C1 gene, particularly the shortened B-peru and/or the shortened C1 of C1-S genes, is preferred, chimeric R, B, or C1 genes can also be used. For instance a chimeric gene can be used which comprises the coding region (e.g. obtained from the cDNA) of any functional R or B gene (i.e. which conditions anthocyanin production anywhere in the plant) which is operably linked to the promoter region of a R or B gene which conditions anthocyanin production in the aleurone (such as R(S) or B-peru). Since the presence of anthocyanin does not negatively affect growth, development and functioning of plant cells, a constitutive promoter (e.g. the 35S promoter), or a promoter which directs expression at least in the aleurone can also be used in such a chimeric gene. In this regard the promoter of the C1 gene can also be used to direct expression of a DNA comprising the coding region of suitable R or B gene, particularly the B-peru gene.

Similarly the coding region (e.g. obtained from cDNA) of the C1 gene can be operably linked to the promoter of a gene that directs expression at least in the aleurone. In this regard, the promoter of the B-peru gene can also be used to direct expression of a DNA comprising the coding region of a suitable C1 gene such as that of the C1 gene of SEQ ID No. 1 or of the C1-S gene.

In another inventive aspect of the invention it was found that the the promoters comprised in DNAs characterized by the sequences between positions 1 to 1077, particularly between positions 447 and 1077, quite particularly between positions 447 and 1061 of SEQ ID NO 1, between positions 396 and 1026 of SEQ ID NO 5, and between positions 1 to 575, particularly between position 1 to 188 of SEQ ID NO 6 are promoters that predominantly, if not selectively, direct expression of any DNA, preferably a heterologous DNA in the aleurone layer of the seeds of plants.

Of course in those lines in which a functional C1 gene is already present in the genome the color gene can consist only of a suitable functional R or B gene (or a chimeric alternative). Alternatively if a line contains already a functional R or B gene which can condition anthocyanin production in the aleurone, but no functional C1 gene, only a functional C1 gene is required as a color gene.

It is believed that the color genes of this invention are especially useful in cereal plants, and that they are of particular use in corn and wheat, and certainly in corn.

For the purposes of this invention it is preferred that, in the second parent plants the "Rf" locus and the male-sterility (e.g. "S") locus are not linked and segregate separately.

In the second parent plant, the fertility restorer gene, the B-peru gene and the C1 gene are preferably closely linked. This can of course be achieved by introducing these genes in the nuclear genome of the plants as a single transforming foreign DNA (the Rf DNA) thus forming a foreign Rf locus. Alternatively, the fertility restorer gene and the color gene can be separately introduced by cotransformation which usually results in single locus insertions in the plant genome.

The color-linked restorer gene Rf as used in the second parent plant preferably also comprises at least c) a second marker gene which comprises at least:

c1) a second marker DNA encoding a second marker RNA, protein or polypeptide which, when present at least in a specific tissue or specific cells of the plant, renders the plant easily separable from other plants which do not contain the second marker RNA, protein or polypeptide encoded by the second marker DNA at least in the specific tissue or specific cells, and, c2) a second marker promoter capable of directing expression of the second marker DNA at least in the specific tissue or specific cells: the second marker DNA being in the same transcriptional unit as, and under the control of, the second marker promoter.

First and second marker DNAs and first and second marker promoters that can be used in the first and second marker genes of this invention are also well known (EP 0,344,029; EP 0,412,911). In this regard it is preferred that the first and second marker DNA are different, although the first and second marker promoter may be the same.

Foreign DNA such as the fertility-restorer gene, the foreign male-sterility gene, the B-peru and the C1 genes, or the first or second marker gene preferably also are provided with suitable 3' transcription regulation sequences and polyadenylation signals, downstream (i.e. 3') from their coding sequence i.e. respectively the fertility-restorer DNA, the male-sterility DNA, the coding region of a color gene (such as a B-peru gene and/or a C1 gene) or the first or second marker DNA. In this regard either foreign or endogenous transcription 3' end formation and polyadenylation signals suitable for obtaining expression of the chimeric gene can be used. For example, the foreign 3' untranslated ends of genes, such as gene 7 (Velten and Schell (1985) Nucl. Acids Res. 13:6998), the octopine synthase gene (De Greve et al., 1982, J.Mol. Appl. Genet. 1:499; Gielen et al (1983) EMBO J. 3:835; Ingelbrecht et al., 1989, The Plant Cell 1:671) and the nopaline synthase gene of the T-DNA region of *Agrobacterium tumefaciens* Ti-plasmid (De Picker et al., 1982, J.Mol. Appl. Genet. 1:561), or the chalcon synthase gene (Sommer and Saedler, 1986, Mol.Gen.Genet. 202:429–434), or the CaMV 19S/35S transcription unit (Mogen et al., 1990, The Plant Cell 2:1261–1272) can be used. However, it is preferred that the color genes in this invention carry their endogenous transcription 3' end formation and polyadenylation signals.

The fertility-restorer gene, the male-sterility gene, the color gene or the first or second marker gene in accordance with the present invention are generally foreign DNAs, preferably foreign chimeric DNA. In this regard "foreign" and "chimeric" with regard to such DNAs have the same meanings as described in EP 0,344,029 and EP 0,412,911.

The cell of a plant, particularly a plant capable of being infected with Agrobacterium such as most dicotyledonous plants (e.g. *Brassica napus*) and some monocotyledonous plants, can be transformed using a vector that is a disarmed Ti-plasmid containing the male-sterility gene, the color linked restorer gene or both and carried by Agrobacterium. This transformation can be carried out using the procedures described, for example, in EP 0,116,718 and EP 0,270,822. Preferred Ti-plasmid vectors contain the foreign DNA between the border sequences, or at least located to the left of the right border sequence, of the T-DNA of the Ti-plasmid. Of course, other types of vectors can be used to transform the plant cell, using procedures such as direct gene transfer (as described, for example, in EP 0,233,247), pollen mediated transformation (as described, for example, in EP 0,270,356, PCT patent publication "WO" 85/01856, and U.S. Pat. No. 4,684,611), plant RNA virus-mediated transformation (as described, for example, in EP 0,067,553 and U.S. Pat. No. 4,407,956) and liposome-mediated transformation (as described, for example, in U.S. Pat. No. 4,536,475). Cells of monocotyledonous plants such as the major cereals including corn, rice, wheat, barley, and rye, can be transformed (e.g. by electroporation) using wounded or enzyme-degraded intact tissues capable of forming compact embryogenic callus (such as immature embryos in corn), or the embryogenic callus (such as type I callus in corn) obtained thereof, as described in WO 92/09696. In case the plant to be transformed is corn, other recently developed methods can also be used such as, for example, the method described for certain lines of corn by From et al., 1990, Bio/Technology 8:833; Gordon-Kamm et al., 1990, Bio/Technology 2:603 and Gould et al., 1991, Plant Physiol. 95:426. In case the plant to be transformed is rice, recently developed methods can also be used such as, for example, the method described for certain lines of rice by Shimamoto et al., 1989, Nature 338:274; Datta et al., 1990, Bio/Technology 8:736; and Hayashimoto et al., 1990, Plant Physiol. 93:857.

The transformed cell can be regenerated into a mature plant and the resulting transformed plant can be used in a conventional breeding scheme to produce more transformed plants with the same characteristics or to introduce the male-sterility gene, the color-linked restorer gene (or both), in other varieties of the same related plant species. Seeds obtained from the transformed plants contain the chimeric gene(s) of this invention as a stable genomic insert. Thus the male-sterility gene, or the color-linked restorer gene of this invention when introduced into a particular line of a plant species can always be introduced into any other line by backcrossing.

The first parent plant of this invention contains the male-sterility gene as a stable insert in its nuclear genome (i.e. it is a male-sterile plant). For the purposes of this invention it is preferred that the first parent plant contains the male-sterility gene in homozygous condition so that it transmits the gene to all of its progeny.

The second parent plant of this invention contains the male-sterility gene and the color-linked restorer gene as stable inserts in its nuclear genome (i.e. it is a restored plant). It is preferred that the male-sterility gene be in homozygous condition so that the second parent plant transmits the gene to all of its progeny and that the color-linked restorer gene be in heterozygous condition so that the second parent plant transmits the gene to only half of its progeny.

It is preferred that the first and second parent plants are produced from the same untransformed line of a plant species, particularly from the same inbred line of that species.

The first and second parent plants of this invention have the particular advantage that seeds of such plants can be maintained indefinitely, and can be amplified to any desired amount (e.g. by continuous crossing of the two plant lines).

The color genes of this invention can be used as marker gene in any situation in which it is worthwhile to detect the presence of a foreign DNA (i.e. a transgene) in seeds of a transformed plant in order to isolate seeds which possess the foreign DNA. In this regard virtually any foreign DNA, particularly a chimeric gene can be linked to the color gene.

Examples of such foreign DNAs are genes coding for insecticidal (e.g. from *Bacillus thuringiensis*), fungicidal or nematocidal proteins. Similarly the color-gene can be linked to a foreign DNA which is the male-sterility gene as used in this invention.

However, the color genes are believed to be of particular use in the process of this invention in which they are present in a foreign DNA which comprises a fertility restorer gene (such as the barstar gene of *Bacillus amylolicruefaciens*) under control of a stamen-specific promoter (such as PTA29). In appropriate conditions the use of the color genes allows the easy separation of harvested seeds that will grow into male-sterile plants, and harvested seeds that will grow into male-fertile plants. In this regard the seeds are preferably harvested from male-sterile plants (the first parent plants) that. are homozygous at a male-sterility locus (such as a locus comprising the barnase gene under control of PTA29) and which have been pollinated by restorer plants (the second parent plants of this invention) which contain in their genome two unlinked gene loci one of which comprises the same male-sterility locus which is homozygous for the same male-sterility gene while the other is a foreign locus which comprises an appropriate fertility restorer gene (i.e. whose expression will counteract the expression of the male-sterility gene) and also the color gene of this invention, particularly an R or B gene that is expressed in the aleurone and/or a C1 gene, preferably the B-peru and C1 gene (e.g. as described in the examples). First and second parent plants can be essentially produced as described in the examples and as summarized in FIG. 1. In step 8 of FIG. 1 it is demonstrated that the crossing of the first and second parent plants of this invention will give rise in the progeny to about 50% new first parent (i.e. male-sterile) plants and about 50% new second parent (i.e. male-fertile) plants and that these two types of plants can already be separated at the seed stage on the basis of color. Red kernels will grow into male-fertile plants while yellow kernels will grow into male-sterile plants.

Thus a line of male-sterile first parent plants of this invention can be easily maintained by continued crossing with the second parent plants of this invention with, in each generation, harvesting the seeds from the male-sterile plants and separation of the yellow and red kernels. Of course in this way any desired amount of seed for foundation seed production of a particular line, such as an inbred line, can also be easily obtained.

The red and yellow seeds harvested from a cereal plant (e.g. the first parent plant of this invention) can be separated manually. However, such separation can also be effected mechanically. A color sorting machine for corn kernel and other granular products is for instance available from Xeltron U.S. (Redmond, Wash., U.S.A.)

Unless otherwise indicated all experimental procedures for manipulating recombinant DNA were carried out by the standardized procedures described in Sambrook et al., 1989, "Molecular Cloning: a Laboratory Manual", Cold Spring Harbor Laboratory, and Ausubel et al, 1994, "Current Protocols in Molecular Biology", John Wiley & Sons.

The polymerase chain reactions ("PCR") were used to clone and/or amplify DNA fragments. PCR with overlap extension was used in order to construct chimeric genes (Horton et al, 1989, Gene 77:61–68; Ho et al, 1989, Gene 77:51–59).

All PCR reactions were performed under conventional conditions using the Vent$^T$M polymerase (Cat. No. 254L—Biolabs New England, Beverley, Mass. 01915, U.S.A.) isolated from *Thermococcus litoralis* (Neuner et al., 1990, Arch.Microbiol. 153:205–207). Oligonucleotides were designed according to known rules as outlined for example by Kramer and Fritz (1968, Methods in Enzymology 154:350), and synthesized by the phosphoramidite method (Beaucage and Caruthers, 1981, Tetrahedron Letters 22:1859) on an applied Biosystems 380A DNA synthesizer (Applied Biosystems B.V., Maarssen, Netherlands).

In the following examples, reference will be made to the following sequence listing and figures:

Sequence Listing
SEQ ID NO 1: sequence of C1 gene
SEQ ID NO 2: plasmid pTS256
SEQ ID NO 3: EcoRI-HindIII region of pTS200 comprising the chimeric gene PCA55-barstar-3'nos (the omitted region of pTS200 is derived from pUC19.
SEQ ID NO 4: oligonucleotide 1
SEQ ID NO 5: pCOL9 containing the shortened C1 gene as a EcoRI-SfiI fragment
SEQ ID NO 6: presumed sequence of the EcoRI-HindIII region of pCOL13 containing the shortened B-peru gene (the rest of the plasmid is pUC19). The stretch of N nucleotides corresponds to a region of approximate length which is derived from the genomic clone of the B-peru gene but for which the sequence needs to be confirmed.
SEQ ID NO 7: actual sequence of the EcoR1-HindIII region of pCOL13 containing the shortened B-peru gene (the rest of the plasmid is pUC19).
Figures
FIG. 1: Breeding scheme to obtain the first and second parent plants of this invention
FIG. 2: Schematic structure of pCOL25, pCOL26, pCOL27, pCOL28, pCOL100 and pDE110.

EXAMPLES

Example 1

Construction of Plasmids Containing the Male-sterility Gene Comprising the TA29 Promoter and the Barnase Coding Region Plasmids useful for transformation of corn plants and carrying a male-sterility gene and a selectable marker gene have been described in WO 92/09696 and WO 92/00275.

Plasmid pVE107 contains the following chimeric genes: 1) PTA29-barnase-3'nos, i.e. a DNA coding for barnase of *Bacillus amyloliquefaciens* (barnase) operably linked to the stamen-specific promoter of the TA29 gene of (neo) operably linked to the 35S promoter of Cauliflower Mosaic Virus (P35S) and the 3' regulatory sequence containing the polyadenylation signal of the octopine synthase gene of *Agrobacterium tumefaciens* (3'ocs).

Plasmid pVE108 contains the following chimeric genes: 1) PTA29-barnase-3'nos, and 2) P35S-bar-3'nos, i.e. the gene of *Streptomyces hygroscopicus* (EP 242236) coding for phosphinothricin acetyl transferase (bar) operably linked to the P35S and 3'nos.

PTA29-barnase-3'nos is an example of a foreign chimeric male-sterility gene (S) used in this invention.

Example 2

Construction of a Plasmid Containing the Color-linked Restorer Gene 2.1. Obtaining a shortened functional C1 gene The C1 gene of maize was cloned from transposable-induced mutants and its sequence was reported (Paz-Ares, 1987, EMBO J. 6:3553–3558). This sequence is reproduced in SEQ ID NO. 1. Plasmid p36 (alternatively designated as pC1LC5kb and further designated as plasmid pXX036) comprising a C1 genomic clone was obtained from Dr. H. Saedler and Dr. U. Wienand of the Max-Planck Institut für Züchtungsforschung, Köln, Germany. pXX036 was digested with SnabI and HindIII, filled-in with Klenow, and selfligated, yielding plasmid pCOL9. pCOL9 corresponds to pUC19 (Yanisch-Perron et al, 1985, Gene 33:103–119) which contains, between its EcoRI and modified HindIII sites, the 2189 bp EcoRI-SnabI fragment (corresponding to the sequence between positions 448 and 2637 of SEQ ID NO 1) of pXX036.

pXX036 was also digested with SfiI and HindIII and treated with Klenow to make blunt ends. After ligation the plasmid in which the DNA downstream from the SfiI site was deleted was designated as pCOL12.

The sequence TGCAG in pCOL9, corresponding to the sequence at positions 884 to 888 in SEQ ID NO 5, is changed to TTAGG, yielding pCOL9S which instead of a shortened C1 gene contains a shortened overexpressing C1-S gene (Schleffer et al, 1994, Mol.Gen.Genet. 242:40–48). A similar change is introduced in pCOL12, yielding pCOL12S.

2.2. Obtaining a shortened functional B-peru gene

Plasmid pBP2 (further designated as pXX004) is plasmid pTZ18U (Mead et al., 1986, Protein Engineering 1:67; U.S. Biochemical Corp.) containing the genomic clone of the B-peru gene. Plasmid p35SBPcDNA (further designated as pXX002) is plasmid pMF6 (Goff et al, 1990, EMBO J. 9:2517–2522) containing the cDNA corresponding to the B-peru gene. Both plasmids were obtained from Dr. V. Chandler of the University of Oregon, Oregon, U.S.A. A 2660 bp sequence of the genomic clone around the translation initiation codon was reported (EMBL/Genbank/DDBJ databases; locus name ZMBPERUA, Accession number X70791; see also Radicella et al, 1992, Genes & Development 6:2152–2164). The sequence of the B-peru cDNA was also reported (Radicella et al, 1991, Plant Mol. Biol. 17:127–130).

Substantial amounts of 5' and 3' flanking sequences were deleted from pXX004, and the MluI-MunI fragment in the coding region of the genomic clone was replaced by the 1615 bp MluI-MunI fragment of the cDNA clone. The resulting plasmid was designated as pCOL13 which was deposited at the Belgian Coordinated Collection of Microorganisms—LMBP Collection, Laboratory Molecular Biology, University of Ghent, K. L. Ledeganckstraat 35, B-9000 Ghent, Belgium and was given the Accession Number LMBP 3041. A shortened but functional B-peru gene is contained in pCOL13 as an EcoRI-SalI fragment with an approximate length of 4 kbp (see SEQ ID NO 6).

2.3. Combining the C1 and B-peru genes

The C1 gene in pCOL9 and the B-peru gene in pCOL13 were then combined as follows. The 4 kbp EcoRI-SalI fragment of pCOL13 was introduced between the EcoRI and SalI sites of the vector pBluescript II SK(−) (Stratagene), yielding #7 B SK(−). pCOL9 was digested with SfiI, treated with Klenow to fill in protruding ends, and further digested with EcoRI. The 1978 bp SfiI(Klenow)/EcoRI was then introduced between the EcoRI and SmaI sites of #7 B SK(−), yielding #7 B+C SK(−). Finally the XhoI site in the C1 sequence was removed as follows. The 950 bp EcoRI-SacII fragment of #7 B SK(−) (EcoRI site corresponding to the EcoRI site at position 1506 in SEQ ID NO 1; the SacII site from the pBluescript linker) was introduced between the EcoRI and SacII sites of the Phagescript Vector (Stratagene) to yield pCOL21. Single strands of pCOL21 were prepared and hybridized to the following synthetic oligonucleotide 1 (SEQ ID No. 4):

5'-CGT TTC TCG AAT CCG ACG AGG-3'
resulting in a silent change (CTCGAG→CTCGAA) and removal of the XhoI site.
The 710 AatII-SacII fragment of #7 B SK(−) was then exchanged for the corresponding AatII-SacII fragment of the mutated pCOL21, yielding pCOL23.
pCOL23 was then linearized with SacII, treated with Klenow, and ligated to XhoI linker sequence (Stratagene), yielding pCOL24.

Using the same procedure as described above, the shortened C1-S gene of pCOL9S is combined with the shortened B-peru gene of pCOL23, yielding plasmid pCOL24S.

2.4. Construction of vectors comprising the C1 and B-peru genes as well as male-sterility gene and a selectable marker gene pTS256 is derived from pUC19 and contains the following two chimeric genes: 1) P35S-bar-3'nos, and 2) PTA29-barstar-3'nos, i.e. a DNA coding for barstar of Bacillus amyloliquefaciens (barstar or bar*) operably linked to PTA29 and 3'nos. The complete sequence of pTS256 is given in SEQ ID NO 2.

pTS200 is derived from pUC19 and contains the following two chimeric genes : 1) P35S-bar-3'nos, and 2) PCA55-barstar-3'nos, i.e. barstar operably linked to the stamen-specific promoter PCA55 of Zea mays and 3'nos. The complete sequence of pTS200 is given in SEQ ID NO 3.

pTS256 was modified by the inclusion of NotI linkers (Stratagene) in both the unique SspI and SmaI sites, yielding pTS256NN. The shorter BspEI-SacII fragment of pTS256NN was then replaced by the shorter BspEI-SacII fragment of pTS200, yielding pTS256+200.

pTS256NN contains P35S-bar3'-nos and pTA29-barstar3'nos on a NotI cassette. pTS256NN+200 contains P35S-bar3'-nos and pCA55-barstar3'nos on a NotI cassette.

he NotI cassette of pTS256NN was introduced in the NotI site of pCOL24, yielding pCOL25 and pCOL26 which differ with respect to the orientation of the P35S-bar3'-nos gene with respect to the shortened C1 gene (FIG. 2).

The NotI cassette of pTS256NN+200 was introduced in the NotI site of pCOL24, yielding pCOL27 and pCOL28 which differ with respect to the orientation of the P35S-bar3'-nos gene with respect to the shortened C1 gene (FIG. 2).

Plasmids pCOL25, pCOL26, pCOL27 or pCOL28 contain a color-linked restorer gene Rf and a selectable marker gene (P35S-bar-3'nos). Rf comprises the shortened C1 and B-peru genes and a chimeric barstar gene (either PTA29-barstar-3'nos or PCA55- barstar-3'nos).

Plasmids pCOL25S, pCOL26S, pCOL27S or pCOL28S, containing the shortened C1-S gene instead of the shortened C1 gene, are obtained in a similar way using pCOL24S instead of PCOL24.

2.5. Construction of vectors comprising the C1 and B-peru genes as well as male-sterility gene Plasmid pTS59 can be obtained from plasmid pTS256 (of SEQ ID NO 2) by replacing the fragment extending from positions 1 to 1470 (comprising the chimeric gene P35S-bar-3'nos) with the sequence TATGATA. Then NotI linkers (Stratagene) were introduced in the EcoRV and SmaI sites of pTS59; yielding pTS59NN. Finally the NotI fragment comprising the chimeric gene PTA29-barstar-3'nos was introduced in the NotI site of #7 B+C SK(−), yielding pCOL100 (the general structure of pCOL100 and pDE110 is also presented in FIG. 2).

2.6. Expression of shortened C1 and B-peru in aleurone in corn seeds

Dry seeds were incubated overnight in water at room temperature and were then peeled and sliced in half. Four to six half kernels were placed with the cut side on wet filter paper and were bombarded with tungsten particles (diameter 0.7 μm) which were coated with DNA.

Particle bombardment was essentially carried out using the particle gun and procedures as described by Zumbrunn et al, 1989, Technique, 1:204–216. The tissue was placed at 10 cm from the stopping plate while a 100 μm mesh was placed at 5 cm from the stopping plate.

DNA of the following plasmids was used:
pXX002: B-peru cDNA under control of the 35S promoter
pXX201: C1 cDNA under control of the 35S promoter pCOL13: shortened B-peru gene as described in Example 2.2
pCOL12: shortened C1 gene as described in Example 2.1
pCOL100: shortened B-peru and shortened C1 and PTA29-barstar-3'nos as described in Example 2.5.

After bombardment the tissue was incubated for 2 days on wet filter paper at 27° C. and was then checked for the presence of red spots indicating anthocyanin production.

TABLE 1

|  |  |  | pXX00 | PXX201 | pXX002 pXX201 | pCOL13 | pCOL12 | pCOL100 |
|---|---|---|---|---|---|---|---|---|
| H99 | r | c1 | − | − | + | nt | nt | nt |
| Pa91 | r | c1 | − | − | + | nt | nt | nt |
| B73 | r | c1 | − | − | + | nt | nt | + |
| inbred1 | r | c1 | − | − | + | nt | nt | nt |
| inbred2 | r | c1 | − | − | + | nt | nt | nt |
| inbred3 | r | c1 | − | − | + | nt | nt | nt |
| inbred4 | r | c1 | + | − | + | + | − | nt |
| inbred5 | r | c1 | + | − | + | + | − | nt |
| inbred6 | r | c1 | − | − | + | nt | nt | nt |
| inbred7 | r | c1 | − | − | + | nt | nt | nt |
| inbred8 | r | c1 | − | − | + | nt | nt | nt |
| inbred9 | r | c1 | + | − | + | + | − | nt |
| c-ruq | R | c1 | − | + | + | − | + | nt |

Note: + indicates that anthocyanin production was observed in at least one experiment;
− indicates that no anthocyanin production was observed,
nt = not tested.

The results for three public lines (H99, Pa91, B73) and 9 different, commercially important, proprietary inbred lines from various sources are shown in Table 1. The line c-ruq is a tester line which is homozygous for a C1 allele that is inactivated by insertion of a receptor for the regulator Uq (Cormack et al., 1988, Crop Sci. 28:941–944).

All lines which were r and c1 produced anthocyanin in the aleurone after introduction with both a functional B-peru and C1 gene. Lines which were R and c1 produced anthocyanin upon introduction of a functional C1 gene. Lines which were r and C1 produced anthocyanin upon introduction of a functional B-peru gene. This proves that the B-peru and C1 gene are sufficient for anthocyanin production in most corn lines. From the data in Table 1 it is also evident that even the shortened B-peru and C1 genes are still functional and are capable of producing anthocyanin in aleurone of corn lines with suitable genotypes.

Example 3
Production of First Parent Corn Plants by Transformation of Corn With the Plasmids of Example 1.

Corn plants of line H99, transformed with a male-sterility gene comprising a DNA encoding barnase of *Bacillus amyloliguefaciens* under control of the promoter of the TA29 gene of *Nicotiana tabacum* have been described in WO 92/09696. The transformed plants were shown to be male-sterile.

Example 4
Production of second Parent Corn Plants by Transformation of Corn With the Plasmids of Examples 2.

Corn inbred lines H99 and Pa91 are transformed using the procedures as described in WO 92/09696 but using plasmids pCOL25, pCOL26, pCOL27 or pCOL28 of Example 2. Regenerated plants are selected that are male fertile and in which the shortened C1, the shortened B-peru gene, the P35S-bar-3'nos gene, and the PTA29-barstar-3'nos (or PCA55-barstar-3'nos) are expressed.

Alternatively the male-sterile plants of Example 3 (already containing the S gene) can be transformed with plasmids pCOL25, pCOL26, pCOL27 or pCOL28 of Example 2 on the condition that the S and Rf genes are linked to different selectable marker genes.

Similarly, transformed corn plants are obtained using plasmids pCOL25S, pCOL26S, pCOL27S or pCOL28S of Example 2.

In an alternative set of experiments the second parent plants of this invention were obtained by transforming corn plants of line H99, Pa91, and (Pa91xH99)x H99 with two separate plasmids one of which contained the color linked restorer gene (pCOL100), while the other contains an appropriate selectable marker gene such as a chimeric bar gene (pDE110) (alternatively a chimeric neo gene may also be used). pDE110 was described in WO 92/09696 and the construction of pCOL100 was descibed in Example 2.5.

In yet another set of experiments the second parent plants of this invention are obtained by transforming corn plants with a purified fragment of the plasmids of example 2.4. Such purified fragment is obtained by digestion of the plasmids of example 2.4 with XhoI and subsequent purification using conventional procedures such as gel filtration.

Untransformed corn plants of lines H99 or Pa91 are detasseled and pollinated with pollen of the plants transformed with the Rf DNA. It is observed that the f gene segregates in a Mendelian way and that the seed that is harvested from these plants is colored and non-colored (yellow) in a 1:1 ratio. The red color of the seeds is correlated with the presence of the Rf gene.

Example 5
The Production of the First and Second Parent Plants of This Invention.

First parent plants and second parent plants (i.e. maintainer plants) according to the invention are produced along the lines set out in FIG. 1.

The male-sterile plants of step 1 are those produced in Example 1. The corn plants transformed with the color-linked restorer gene of step 2 are those produced in Example 4.

A plant of Example 1 and a plant of Example 4 are crossed (Step 3) and the progeny plants with the genotype S/-, Rf/- are selected (Step 4), e.g. by demonstrating the presence of both the S and Rf genes in the nuclear genome (e.g. by means of PCR).

The plants selected in Step 4 are then crossed with the male-sterile plants with genotype S/- (Step 5). The colored seeds (i.e. those containing the Rf gene) are selected, grown into plants, and examined for the presence of both the S and Rf genes (e.g. by PCR). The plants containing both the S and Rf genes are selfed and the seeds of each plant are examined on seed color (red or yellow). From the progeny of the selfings the non-colored seeds are grown into plants (Step 6). The progeny of the selfings in which all noncolored seeds grow into male-sterile plants are retained (Step 6). These male-sterile plants are all homozygous for the S gene and are crossed with their fertile siblings (of genotype S/S,Rf/Rf or S/S,Rf/-) (Step 7). For some crossings the seeds harvested from the male-sterile plants are 50% colored and 50% non-colored (step 7). The colored seeds all grow into fertile corn plants of genotype S/S,Rf/- which are the maintainer plants, or the second parent plants, of the present invention. The noncolored seeds all grow into male-sterile plants of the genotype S/S,-/- which are the first parent plants of this invention (Step 7).

The first and second parent plants are crossed and the seeds harvested from the male-sterile plants are separated on the basis of color (Step 8). All colored seeds grow again in second parent plants and all noncolored seeds grow in first parent plants, thereby establishing an easy maintenance of a pure male-sterile line of corn.

If the plant DNA that is flanking the s gene in the plants of Example 1 has been characterized, the progeny of the cross in Step 5 with genotypes S/S,-/- and S/S,R/- can be easily identified by means of PCR using probes corresponding to the flanking plant DNA. In this way Step 6 can be skipped because the plants of Step 5 which grow from colored seeds (genotype S/S,Rf/-) can be crossed directly to plants with genotype S/S,-/- (as in Step 7).

All publications cited in this application are hereby incorporated by reference.

Example 6
Maintainer Slants Containing a Color-linked Restorer Gene Comprising the B-Peru Coding Region Under control of the Promoter of the C1-S Gene.

Using conventional techniques a chimeric gene is inserted between the EcoRI and HindIII sites of the polylinker of plasmid pUC19. The chimeric gene comprises the following elements in sequence:

i) the promoter region of the C1-S gene, i.e. the DNA fragment with the sequence of SEQ ID No. 1 from nucleotide positions 447 up to 1076 but containing at nucleotide positions 935–939 the sequence TTAG instead of TGCAG.

ii) a single C nucleotide iii) the coding region and 3'untranslated region of the B-peru gene, i.e. the DNA fragment with the sequence of SEQ ID No. 7 from nucleotide positions 576 up to 4137.

This plasmid (designated as pLH52), together with plasmid pCOL9S of Example 2 (comprising a C1-S gene) and pTS256 of SEQ ID No. 2 (comprising the following chimeric genes: P35S-bar-3'nos and PTA29-barstar-3'nos), is used to transform corn essentially as described in Example 4. The transformed plants are then used to obtain second parent plants as described in Example 5.

Example 7
Maintainer Plants Containing a Color-linked Restorer Gene Comprising the B-Peru Coding Region Under Control of the 35S Promoter.

Using conventional techniques a chimeric gene is inserted between the EcoRI and HindIII sites of the polylinker of plasmid pUC19. The chimeric gene comprises the following elements in sequence:

i) The promoter region of the 35S promoter, i.e. the DNA fragment of pDE110 which essentially has the sequence as described in SEQ ID No. 4 of WO 92/09696 (which is incorporated herein by reference) from nucleotide positions 396 up to 1779 ii) the coding region and 3'untranslated region of the B-peru gene, i.e. the DNA fragment with the sequence of SEQ ID No. 7 from nucleotide positions 576 up to 4137.

This plasmid (designated as pP35S-Bp), together with plasmid pCOL9S of Example 2 (comprising a C1-S gene) and pTS256 of SEQ ID No. 2 (comprising the following chimeric genes: P35S-bar-3'nos and PTA-29-bar-3'nos), is used to transform corn essentially as described in Example 4. The transformed plants are then used to obtain second parent plants as described in Example 5.

Alternatively plasmid p35SBperu as described in Goff et al, 1990, EMBO 9:2517–2522 is used instead of pP35SBp.

Example 8
Maintainer Plants Containing a Color-linked Restorer Gene Comprising the Maize P Gene Coding Region Under the Controls the Promoter of the C1-S Gene.

Using conventional techniques a chimeric gene is inserted in the EcoRI site of the polylinker of plasmid pUC19. The chimeric gene comprises the following elements in sequence;

i) the promoter region of the C1-S gene, i.e. the DNA fragment with the sequence of SEQ ID No. 1 for nucleotide positions 447 up to 1076 but containing at nucleotide positions 935–939 the sequence TTAGG instead of TGCAG:

ii) a single C nucleotide;

iii) a DNA sequence comprising the coding region and 3'end untranslated region of the maize P gene as described by Grotewold et al in 1991, PNAS 88:4587–4591 (nucleotides 320–1517). The maize P gene is an anthocyanin regulatory gene which specifies red phlobaphene pigmentation, a flavonoid pigment involved in the biosynthesis pathway of anthocyanin. In fact, the protein encoded by the P gene activates, among others, the A1 gene required for both anthocyanin and phlobaphene pigmentation. Two cDNA clones have been isolated and sequenced by Grotewold et al and are described in the publication referred to above. It is the longer cDNA which is of particular interest for construction of this chimeric gene. However, alternatively, the coding region of the shorter transcript can also be used in this chimeric gene, as well as the P gene leader sequence instead of the CI-S gene leader sequence. The P gene does not require a functional R or B gene to produce pigmentation. The visible pigment that is produced in the seeds of the maintainer plants is phlobaphene, a flavonoid pigment (like anthocyanin) directly involved in anthocyanin biosynthesis.

iv) a DNA fragment containing the polyadenylation signal of the nopaline synthase gene of *Agrobacterium tumefaciens*, i.e. the DNA fragment with the sequence of SEQ ID. No. 2 from nucleotide position 1600 up to nucleotide position 2909.

The resulting plasmid (designated as pPCS1-P), together with pTS256 of SEQ ID No. 2 is used to transform corn essentially as described in example 4. The transformed plants are then used to obtain second parent plants as described in example 5.

Example 9
Maintainer Plants Containing a Color-linked Restorer Gene Comprising the B-peru Coding Region Under the Control of the B-peru Promoter.

Using conventional techniques a chimeric gene is inserted between the EcoR1 and the HindIII sites of the polylinker of plasmid pUC19. The chimeric gene comprises the following elements in sequence:

i) the promoter of the B-peru gene, i.e. a 1952 bp DNA sequence as disclosed in the EMBL databank under accession number X70791;

ii) the coding region and 3'untranslated region of the B-peru gene, i.e. the DNA fragment with the sequence of SEQ ID No. 7 from nucleotide position 576 up to 4137. This plasmid (designated aspCOL11), together with plasmid pCOL 9S of example 2 (comprising a C1-S gene) and pTS256 of SEQ ID No. 2 (comprising the following chimeric genes: P35S-bar-3'nos and PTA29-barstar-3'nos) is used to transform corn essentially as described in example 4. The transformed plants are then used to obtain second parent plants as described in example 5.

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 4059 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: C1 gene of Zea mays ( i x ) FEATURE:
        ( A ) NAME/KEY: -
        ( B ) LOCATION: 279..284
        ( D ) OTHER INFORMATION: /label=HpaI ( i x ) FEATURE:
        ( A ) NAME/KEY: -
        ( B ) LOCATION: 447..452
        ( D ) OTHER INFORMATION: /label=EcoRI ( i x ) FEATURE:
        ( A ) NAME/KEY: -
        ( B ) LOCATION: 1735..1740
        ( D ) OTHER INFORMATION: /label=AatII ( i x ) FEATURE:
        ( A ) NAME/KEY: -
        ( B ) LOCATION: 1505..1510
        ( D ) OTHER INFORMATION: /label=EcoRI ( i x ) FEATURE:
        ( A ) NAME/KEY: -
        ( B ) LOCATION: 2081..2086
        ( D ) OTHER INFORMATION: /label=XhoI ( i x ) FEATURE:
        ( A ) NAME/KEY: -
        ( B ) LOCATION: 2418..2430
        ( D ) OTHER INFORMATION: /label=SfiI ( i x ) FEATURE:
        ( A ) NAME/KEY: -
        ( B ) LOCATION: 2669..2674
        ( D ) OTHER INFORMATION: /label=SnaBI ( i x ) FEATURE:
        ( A ) NAME/KEY: -
        ( B ) LOCATION: 2634..2639
        ( D ) OTHER INFORMATION: /label=SnaBI ( i x ) FEATURE:
        ( A ) NAME/KEY: -
        ( B ) LOCATION: 3008..3013
        ( D ) OTHER INFORMATION: /label=HpaI ( i x ) FEATURE:

( A ) NAME/KEY: -
            ( B ) LOCATION: 1..1077
            ( D ) OTHER INFORMATION: /label=PC1
                    / note= "region containing promoter of C1 gene"

( i x ) FEATURE:
            ( A ) NAME/KEY: -
            ( B ) LOCATION: 1078..2134
            ( D ) OTHER INFORMATION: /label=C1
                    / note= "coding region of C1 gene"

( i x ) FEATURE:
            ( A ) NAME/KEY: -
            ( B ) LOCATION: 2135..2430
            ( D ) OTHER INFORMATION: /label=3'C1
                    / note= "region containing polyadenylation signal
                    of C1 gene"

( i x ) FEATURE:
            ( A ) NAME/KEY: -
            ( B ) LOCATION: 1033..1038
            ( D ) OTHER INFORMATION: /label=TATA-Box ( i x ) FEATURE:
            ( A ) NAME/KEY: -
            ( B ) LOCATION: 1061..1062
            ( D ) OTHER INFORMATION: /label=transcript-init
                    / note= "transcription initiation site"

( i x ) FEATURE:
            ( A ) NAME/KEY: intron
            ( B ) LOCATION: 1211..1299

( i x ) FEATURE:
            ( A ) NAME/KEY: intron
            ( B ) LOCATION: 1430..1575

( i x ) FEATURE:
            ( A ) NAME/KEY: -
            ( B ) LOCATION: 935..939
            ( D ) OTHER INFORMATION: /label= C1- S
                    / note= "TGCAG sequence (in C1 gene) which in the
                    C1-S sequence is changed to TTAGG"

( x i ) SEQUENCE DESCRIPTION: SEQ ID NO:1:

| | | | | | | |
|---|---|---|---|---|---|---|
| TATCAACCTC | CTGTGTTATT | TTTAGTGACG | GTTTCTTAAA | AAACACCACT | AGAAATCGTA | 60 |
| TTTTTATAGG | TGGTTCCTTA | AGAAAACTGC | ATGCAGAAAT | CCATGACGGT | TTTCTTAAGG | 120 |
| AACCGTATGT | AGAAATACGA | TTTCTAGTGA | CGATCTTCTT | AAGGAAACCA | CCACTAAAAA | 180 |
| TTATTTTTAT | CCTTAATTTT | CGAGTTTTTC | AAACGATCTC | GTATGATGAA | ACCATCAAAA | 240 |
| TAAAAGTTGT | ACATCTCTAA | AAGTTATGAA | AATTTGTAGT | TAACAACTTT | TTTATTTGAA | 300 |
| CTCATTTTGG | TTCTCAAAAA | TTGCATCTAA | ATTTGTCAAA | TTTAAAATTC | AAATTTTCCA | 360 |
| AACGACCTCG | GATGAAAAAA | GTGTCAAAAT | GAAAGTTGTA | GAACTTCAAA | AGTTATTCAA | 420 |
| CTTTGTAGTC | GACTATCTTT | TTATTTGAAT | TCGCTTACGG | TCTCAAACAA | GCAATTTACA | 480 |
| CTCAGTTGGT | TGTAATATGT | GGACAATAAA | ACTACAAACT | AGACACAAAT | CATACCATAG | 540 |
| ACGGAGTGGT | AGCAGAGGGT | ACGCGCGAGG | GTGAGATAGA | GGATTCTCCT | AAAATAAATG | 600 |
| CACTTTAGAT | GGGTAGGGTG | GGGTGAGGCC | TCTCCTAAAA | TGAAACTCGT | TTAATGTTTC | 660 |
| TAAAAATAGT | TTTCACTGGT | GATCCTTAGT | TACTGGCATG | TAAAAATGAT | GATTTCTACT | 720 |
| GTCTCTCATA | TGGACGGTTA | TAAAAAATAC | CATTATATTG | AAAATAGGTC | TCTGCTGCTA | 780 |
| CACTCGCCCT | CATAGCAGAT | CATGCATGCA | CGCATCATTC | GATCAGTTTT | CGTTCTGATG | 840 |
| CAGTTTTCGA | TAAATGCCAA | TTTTTTAACT | GCATACGTTG | CCCTTGCTCA | GCACCAGCAC | 900 |
| AGCAGTGTCG | TGTCGTCCAT | GCATGCACTT | TAGGTGCAGT | GCAGGGCCTC | AACTCGGCCA | 960 |
| CGTAGTTAGC | GCCACTGCTA | CAGATCGAGG | CACCGGTCAG | CCGGCCACGC | ACGTCGACCG | 1020 |

| | | | | | | |
|---|---|---|---|---|---|---|
| CGCGCGTGCA | TTTAAATACG | CCGACGACGG | AGCTTGATCG | ACGAGAGAGC | GAGCGCGATG | 1080 |
| GGGAGGAGGG | CGTGTTGCGC | GAAGGAAGGC | GTTAAGAGAG | GGGCGTGGAC | GAGCAAGGAG | 1140 |
| GACGATGCCT | TGGCCGCCTA | CGTCAAGGCC | CATGGCGAAG | GCAAATGGAG | GGAAGTGCCC | 1200 |
| CAGAAAGCCG | GTAAAACTAG | CTAGTCTTTT | TATTTCATTT | TGGGATCATA | TATATACCCC | 1260 |
| CGAGGCAAGA | CCGGAGGACG | ATCACGTGTG | TGGGTGCAGG | TTTGCGTCGG | TGCGGCAAGA | 1320 |
| GCTGCCGGCT | GCGGTGGCTG | AACTACCTCC | GGCCCAACAT | CAGGCGCGGC | AACATCTCCT | 1380 |
| ACGACGAGGA | GGATCTCATC | ATCCGCCTCC | ACAGGCTCCT | CGGCAACAGG | TCTGTGCAGT | 1440 |
| GGCCAGTGGT | GGGCTAGCTT | ATTACACGAG | CTGACGACGA | GGCGATCGAT | CGAGCGTCTG | 1500 |
| CTGCGAATTC | ATCTGTTCCG | GTGTCGGCCG | TGTGAGAGTG | AGCTCATTCA | TATGTACATG | 1560 |
| CGTGTTGGCG | CGCAGGTGGT | CGCTGATTGC | AGGCAGGCTC | CCTGGCCGAA | CAGACAATGA | 1620 |
| AATCAAGAAC | TACTGGAACA | GCACGCTGGG | CCGGAGGGCA | GGCGCCGGCG | CCGGCGCCGG | 1680 |
| CGGCAGCTGG | GTCGTCGTCG | CGCCGGACAC | CGGCTCGCAC | GCCACCCCGG | CCGCGACGTC | 1740 |
| GGGCGCCTGC | GAGACCGGCC | AGAATAGCGC | CGCTCATCGC | GCGGACCCCG | ACTCAGCCGG | 1800 |
| GACGACGACG | ACCTCGGCGG | CGGCGGTGTG | GGCGCCCAAG | GCCGTGCGGT | GCACGGGCGG | 1860 |
| ACTCTTCTTC | TTCCACCGGG | ACACGACGCC | GGCGCACGCG | GGCGAGACGG | CGACGCCAAT | 1920 |
| GGCCGGTGGA | GGTGGAGGAG | GAGGAGGAGA | AGCAGGGTCG | TCGGACGACT | GCAGCTCGGC | 1980 |
| GGCGTCGGTA | TCGCTTCGCG | TCGGAAGCCA | CGACGAGCCG | TGCTTCTCCG | GCGACGGTGA | 2040 |
| CGGCGACTGG | ATGGACGACG | TGAGGGCCCT | GGCGTCGTTT | CTCGAGTCCG | ACGAGGACTG | 2100 |
| GCTCCGCTGT | CAGACGGCCG | GGCAGCTTGC | GTAGACAACA | AGTACACGTA | TAGATGTCCA | 2160 |
| ATAAGCACGA | GGCCCGCGAG | CCCGGCACGA | AGCCCGCTTT | TTGGGCCCGG | TCCGAGCCCG | 2220 |
| GCACGGCCCG | GTTATATGCA | GACCCGGGCC | GGCCCGGCAC | GAATAAGCGG | GCCGGGCTCG | 2280 |
| GACAGGAAAT | TAGGCACGGT | GAGCTAGCCC | GGCACGGCCC | GTTAGGTCT | AAGCCCGTTA | 2340 |
| AGCCCGTTTT | TTTACACTAA | AACGTGCTTC | TCGGCCCGCA | TAGCCCGCTT | CTCGGCCCGC | 2400 |
| TTTTTTCGTG | CTAAACGGGC | CGGCCCGGCC | CGGTTTAGGC | CCGTTGCGGG | CCGGGCTCGG | 2460 |
| ACAGGAAATT | GAGCCCGCGT | GCTTAGCCGG | CCCGGCCCGG | TTTTTTAATC | GTGCCTGGCG | 2520 |
| GGCCAGGCCC | AAAACGGGCC | GGGCTTCACC | GGGCCCGGGC | CGGACCGGGC | CGGGCGGCCC | 2580 |
| GTTTGGACAT | CTCTAAGTAC | ACGTATGGAG | GAGAATATAT | ATATAGTCAT | GCGTACGTAT | 2640 |
| AGATTTTTTC | ATCCGATCCC | AACAGAAATA | CGTATGAAAA | TGCTCTTCGT | TCTTTTTCAT | 2700 |
| TTATCATATC | TATACTATAC | TTAAAACACC | AGTTTCAACG | GTCGTCATGC | GTCATTTTTT | 2760 |
| TACAAATAAC | CCCTCACAGC | TATTTCAAAT | TAATCCGCTG | CACGTCTATA | GATGCCAAAC | 2820 |
| GACGCCCAAC | ACGGGCTAGA | TGCACGCGGG | CCACAACTAT | GGCACAGGCA | CGTCATGCCG | 2880 |
| GCCTGCTAAC | TGTGTCGGGC | TAGCCCGTTA | GCCCGTCGAT | CCATTTAATT | AAATTAGCGT | 2940 |
| AACGACGCCC | GACACGGGCT | AGATGCACGT | GGGCCACAAC | TATGGCACAT | GCACGTCATG | 3000 |
| CCGGCCTGTT | AACTGTGTCG | GGCCAGTCTG | TTAGCCCATT | GATCCATTTA | ATTAAATCAG | 3060 |
| CGTAAAATGT | TAAAAACGGT | GCAGGAGGTG | GGGTTCGAAC | CCATACCCTG | ATGGAAGAAG | 3120 |
| GGCGGGAGAC | ACTGGGTGAA | ACTGTCTAAC | CAGTAGAATA | TCTATCACGC | TAAGATGTTT | 3180 |
| TTAATATTGA | ATATAAATTG | TATATAAGCA | TATAAGTTTT | TTTGTAAAAT | AAAAAATAAT | 3240 |
| CGTGTCGGGC | CGGGCCATCA | CTACTGGCCG | AGGCTACAAC | CCAAGCACGA | CACGACGTTC | 3300 |
| TTGGCTCTTG | CAAGCATTAG | GTCGTTTCTG | AGACCATATT | GGCGCAATGG | ACTACATGAT | 3360 |
| GTTTGGGGTT | GCTGAATTGA | ATGGAGCAGC | AATAATTTGT | CACACTAACA | GCAAAATGAA | 3420 |

-continued

| | | | | | |
|---|---|---|---|---|---|
| AGGTTATTTG | TTGGTTTTAA | ACGTTAGTAA | TTGCTACGAA | GTAGCATAAT | TTATATGGAG | 3480 |
| CGCATCCAGT | TTTTATTGAT | GCCTGACTTT | AGCAATCACT | CCATATTTTG | ATCTATCTTT | 3540 |
| TTTATAAGTT | TGACTTCATG | GGACTTATTT | TAGAACTTGA | TCTCACAAAC | TTTCTCTTAT | 3600 |
| TTTGTCTCTA | TATGATGAAA | TTGTGTCATT | TTATAATCTT | TGTTCATTCA | GTCAATCGTT | 3660 |
| GTGAACTCTC | TTCTAATCAC | TCACTTCATT | AGTTGTGTTG | TACCAAGACA | TATTTGCATA | 3720 |
| GAGTAAACAA | TAACATCAGT | TAGCCAAATC | AAAAAATATA | TTATACAGAG | AGCGGAGACA | 3780 |
| ATCAAATAAA | AAATCTTGAA | ATTTTTTTAA | TGGATAGTTT | ACGTGGGTAT | TGTTGTAAGC | 3840 |
| CGTCGCAACG | CACGGGCAAC | CGACTAGTTT | TAGTTTATAA | ATTAATAAAC | GTACGACAAA | 3900 |
| TATTAAGAAC | GCCACCTTTC | CATGCCTACG | CGCGCGTGAG | ACACGACCGG | GGCACGTCAG | 3960 |
| ACGTGTGCCC | CTGTTGTATA | ATTTATTTAC | TTTTTAATGA | CTATGTGCTG | TTGGTTGCCG | 4020 |
| TTGGCTTCAT | CGTGTTCGTA | GCCATGCATA | AATCCAGCG | | | 4059 |

( 2 ) INFORMATION FOR SEQ ID NO:2:

( i ) SEQUENCE CHARACTERISTICS:
        ( A ) LENGTH: 4896 base pairs
        ( B ) TYPE: nucleic acid
        ( C ) STRANDEDNESS: double
        ( D ) TOPOLOGY: circular ( i i ) MOLECULE TYPE: DNA (genomic)

( v i ) ORIGINAL SOURCE:
        ( A ) ORGANISM: plasmid pTS256, linearized at HindIII ( i x ) FEATURE:
        ( A ) NAME/KEY: -
        ( B ) LOCATION: complement (39..317)
        ( D ) OTHER INFORMATION: /label=3'nos
            / note= "3'regulatory sequence containing the
            polyadenylation signal of the nopaline synthase
            gene of Agrobacterium T-DNA"

( i x ) FEATURE:
        ( A ) NAME/KEY: -
        ( B ) LOCATION: complement (318..869)
        ( D ) OTHER INFORMATION: /label=bar
            / note= "coding region of bar gene of Streptomyces
            hygroscopicus"

( i x ) FEATURE:
        ( A ) NAME/KEY: -
        ( B ) LOCATION: complement (870..1702)
        ( D ) OTHER INFORMATION: /label=P35S
            / note= "35S promoter of Cauliflower Mosaic Virus"

( i x ) FEATURE:
        ( A ) NAME/KEY: -
        ( B ) LOCATION: 1740..2284
        ( D ) OTHER INFORMATION: /label=PTA29
            / note= "promoter of TA29 gene of Nicotiana
            tabacum"

( i x ) FEATURE:
        ( A ) NAME/KEY: -
        ( B ) LOCATION: 2285..2557
        ( D ) OTHER INFORMATION: /label=barstar
            / note= "coding region of barstar gene of Bacillus
            amyloliquefaciens"

( i x ) FEATURE:
        ( A ) NAME/KEY: -
        ( B ) LOCATION: 2558..2879
        ( D ) OTHER INFORMATION: /label=3'nos
            / note= "3'regulatory sequence containing the
            polyadenylation signal of the nopaline synthase
            gene of Agrobacterium T-DNA"

( i x ) FEATURE:

(A) NAME/KEY: -
(B) LOCATION: 1..38
(D) OTHER INFORMATION: /label=pUC19
/ note= "pUC19 derived sequence"

(ix) FEATURE:
(A) NAME/KEY: -
(B) LOCATION: 2880..4896
(D) OTHER INFORMATION: /label=pUC19
/ note= "pUC19 derived sequence"

(ix) FEATURE:
(A) NAME/KEY: -
(B) LOCATION: 3004..3009
(D) OTHER INFORMATION: /label=EcoRI (xi) SEQUENCE DESCRIPTION: SEQ ID NO:2:

| | | | | | | |
|---|---|---|---|---|---|---|
| CAGCTTGCAT | GCCTGCAGGT | CGACTCTAGA | GGATCTTCCC | GATCTAGTAA | CATAGATGAC | 60 |
| ACCGCGCGCG | ATAATTTATC | CTAGTTTGCG | CGCTATATTT | TGTTTTCTAT | CGCGTATTAA | 120 |
| ATGTTATAAT | GCGGGACTCT | AATCATAAAA | ACCCATCTCA | TAAATAACGT | CATGCATTAC | 180 |
| ATGTTAATTA | TTACATGCTT | AACGTAATTC | AACAGAAATT | ATATGATAAT | CATCGCAAGA | 240 |
| CCGGCAACAG | GATTCAATCT | TAAGAAACTT | TATTGCCAAA | TGTTTGAACG | ATCTGCTTCG | 300 |
| GATCCTAGAC | GCGTGAGATC | AGATCTCGGT | GACGGGCAGG | ACCGGACGGG | GCGGTACCGG | 360 |
| CAGGCTGAAG | TCCAGCTGCC | AGAAACCCAC | GTCATGCCAG | TTCCCGTGCT | TGAAGCCGGC | 420 |
| CGCCCGCAGC | ATGCCGCGGG | GGGCATATCC | GAGCGCCTCG | TGCATGCGCA | CGCTCGGGTC | 480 |
| GTTGGGCAGC | CCGATGACAG | CGACCACGCT | CTTGAAGCCC | TGTGCCTCCA | GGGACTTCAG | 540 |
| CAGGTGGGTG | TAGAGCGTGG | AGCCCAGTCC | CGTCCGCTGG | TGGCGGGGGG | AGACGTACAC | 600 |
| GGTCGACTCG | GCCGTCCAGT | CGTAGGCGTT | GCGTGCCTTC | CAGGGGCCCG | CGTAGGCGAT | 660 |
| GCCGGCGACC | TCGCCGTCCA | CCTCGGCGAC | GAGCCAGGGA | TAGCGCTCCC | GCAGACGGAC | 720 |
| GAGGTCGTCC | GTCCACTCCT | GCGGTTCCTG | CGGCTCGGTA | CGGAAGTTGA | CCGTGCTTGT | 780 |
| CTCGATGTAG | TGGTTGACGA | TGGTGCAGAC | CGCCGGCATG | TCCGCCTCGG | TGGCACGGCG | 840 |
| GATGTCGGCC | GGGCGTCGTT | CTGGGTCCAT | GGTTATAGAG | AGAGAGATAG | ATTTATAGAG | 900 |
| AGAGACTGGT | GATTTCAGCG | TGTCCTCTCC | AAATGAAATG | AACTTCCTTA | TATAGAGGAA | 960 |
| GGGTCTTGCG | AAGGATAGTG | GGATTGTGCG | TCATCCCTTA | CGTCAGTGGA | GATGTCACAT | 1020 |
| CAATCCACTT | GCTTTGAAGA | CGTGGTTGGA | ACGTCTTCTT | TTTCCACGAT | GCTCCTCGTG | 1080 |
| GGTGGGGGTC | CATCTTTGGG | ACCACTGTCG | GCAGAGGCAT | CTTGAATGAT | AGCCTTTCCT | 1140 |
| TTATCGCAAT | GATGGCATTT | GTAGGAGCCA | CCTTCCTTTT | CTACTGTCCT | TTCGATGAAG | 1200 |
| TGACAGATAG | CTGGGCAATG | GAATCCGAGG | AGGTTTCCCG | AAATTATCCT | TTGTTGAAAA | 1260 |
| GTCTCAATAG | CCCTTTGGTC | TTCTGAGACT | GTATCTTTGA | CATTTTTGGA | GTAGACCAGA | 1320 |
| GTGTCGTGCT | CCACCATGTT | GACGAAGATT | TTCTTCTTGT | CATTGAGTCG | TAAAAGACTC | 1380 |
| TGTATGAACT | GTTCGCCAGT | CTTCACGGCG | AGTTCTGTTA | GATCCTCGAT | TTGAATCTTA | 1440 |
| GACTCCATGC | ATGGCCTTAG | ATTCAGTAGG | AACTACCTTT | TTAGAGACTC | CAATCTCTAT | 1500 |
| TACTTGCCTT | GGTTTATGAA | GCAAGCCTTG | AATCGTCCAT | ACTGGAATAG | TACTTCTGAT | 1560 |
| CTTGAGAAAT | ATGTCTTTCT | CTGTGTTCTT | GATGCAATTA | GTCCTGAATC | TTTTGACTGC | 1620 |
| ATCTTTAACC | TTCTTGGGAA | GGTATTTGAT | CTCCTGGAGA | TTGTTACTCG | GGTAGATCGT | 1680 |
| CTTGATGAGA | CCTGCTGCGT | AGGAGCTTGC | ATGCCTGCAG | GTCGACTCTA | GAGGATCCCC | 1740 |
| ATCTAGCTAA | GTATAACTGG | ATAATTTGCA | TTAACAGATT | GAATATAGTC | GCAAACAAGA | 1800 |
| AGGGACAATT | GACTTGTCAC | TTTATGAAAG | ATGATTCAAA | CATGATTTTT | TATGTACTAA | 1860 |

| | | | | | | |
|---|---|---|---|---|---|---|
| TATATACATC | CTACTCGAAT | TAAAGCGACA | TAGGCTCGAA | GTATGCACAT | TTAGCAATGT | 1920 |
| AAATTAAATC | AGTTTTTGAA | TCAAGCTAAA | AGCAGACTTG | CATAAGGTGG | GTGGCTGGAC | 1980 |
| TAGAATAAAC | ATCTTCTCTA | GCACAGCTTC | ATAATGTAAT | TTCCATAACT | GAAATCAGGG | 2040 |
| TGAGACAAAA | TTTTGGTACT | TTTTCCTCAC | ACTAAGTCCA | TGTTTGCAAC | AAATTAATAC | 2100 |
| ATGAAACCTT | AATGTTACCC | TCAGATTAGC | CTGCTACTCC | CCATTTTCCT | CGAAATGCTC | 2160 |
| CAACAAAAGT | TAGTTTTGCA | AGTTGTTGTG | TATGTCTTGT | GCTCTATATA | TGCCCTTGTG | 2220 |
| GTGCAAGTGT | AACAGTACAA | CATCATCACT | CAAATCAAAG | TTTTACTTA | AAGAAATTAG | 2280 |
| CTACCATGAA | AAAAGCAGTC | ATTAACGGGG | AACAAATCAG | AAGTATCAGC | GACCTCCACC | 2340 |
| AGACATTGAA | AAAGGAGCTT | GCCCTTCCGG | AATACTACGG | TGAAAACCTG | GACGCTTTAT | 2400 |
| GGGATTGTCT | GACCGGATGG | GTGGAGTACC | CGCTCGTTTT | GGAATGGAGG | CAGTTTGAAC | 2460 |
| AAAGCAAGCA | GCTGACTGAA | AATGGCGCCG | AGAGTGTGCT | TCAGGTTTTC | CGTGAAGCGA | 2520 |
| AAGCGGAAGG | CTGCGACATC | ACCATCATAC | TTTCTTAATA | CGATCAATGG | GAGATGAACA | 2580 |
| ATATGGAAAC | ACAAACCCGC | AAGCTTGGTC | TAGAGGATCC | GAAGCAGATC | GTTCAAACAT | 2640 |
| TTGGCAATAA | AGTTTCTTAA | GATTGAATCC | TGTTGCCGGT | CTTGCGATGA | TTATCATATA | 2700 |
| ATTTCTGTTG | AATTACGTTA | AGCATGTAAT | AATTAACATG | TAATGCATGA | CGTTATTTAT | 2760 |
| GAGATGGGTT | TTTATGATTA | GAGTCCCGCA | ATTATACATT | TAATACGCGA | TAGAAAACAA | 2820 |
| AATATAGCGC | GCAAACTAGG | ATAAATTATC | GCGCGCGGTG | TCATCTATGT | TACTAGATCG | 2880 |
| GGAAGATCCC | CGGGTACCGA | GCTCGAATTC | TGATCAGGCC | AACGCGCGGG | GAGAGGCGGT | 2940 |
| TTGCGTATTG | GGCGCTCTTC | CGCTTCCTCG | CTCACTGACT | CGCTGCGCTC | GGTCGTTCGG | 3000 |
| CTGCGGCGAG | CGGTATCAGC | TCACTCAAAG | GCGGTAATAC | GGTTATCCAC | AGAATCAGGG | 3060 |
| GATAACGCAG | GAAAGAACAT | GTGAGCAAAA | GGCCAGCAAA | AGGCCAGGAA | CCGTAAAAAG | 3120 |
| GCCGCGTTGC | TGGCGTTTTT | CCATAGGCTC | CGCCCCCCTG | ACGAGCATCA | CAAAAATCGA | 3180 |
| CGCTCAAGTC | AGAGGTGGCG | AAACCCGACA | GGACTATAAA | GATACCAGGC | GTTTCCCCCT | 3240 |
| GGAAGCTCCC | TCGTGCGCTC | TCCTGTTCCG | ACCCTGCCGC | TTACCGGATA | CCTGTCCGCC | 3300 |
| TTTCTCCCTT | CGGGAAGCGT | GGCGCTTTCT | CAATGCTCAC | GCTGTAGGTA | TCTCAGTTCG | 3360 |
| GTGTAGGTCG | TTCGCTCCAA | GCTGGGCTGT | GTGCACGAAC | CCCCCGTTCA | GCCCGACCGC | 3420 |
| TGCGCCTTAT | CCGGTAACTA | TCGTCTTGAG | TCCAACCCGG | TAAGACACGA | CTTATCGCCA | 3480 |
| CTGGCAGCAG | CCACTGGTAA | CAGGATTAGC | AGAGCGAGGT | ATGTAGGCGG | TGCTACAGAG | 3540 |
| TTCTTGAAGT | GGTGGCCTAA | CTACGGCTAC | ACTAGAAGGA | CAGTATTTGG | TATCTGCGCT | 3600 |
| CTGCTGAAGC | CAGTTACCTT | CGGAAAAAGA | GTTGGTAGCT | CTTGATCCGG | CAAACAAACC | 3660 |
| ACCGCTGGTA | GCGGTGGTTT | TTTTGTTTGC | AAGCAGCAGA | TTACGCGCAG | AAAAAAAGGA | 3720 |
| TCTCAAGAAG | ATCCTTTGAT | CTTTTCTACG | GGGTCTGACG | CTCAGTGGAA | CGAAAACTCA | 3780 |
| CGTTAAGGGA | TTTTGGTCAT | GAGACTCGAG | CCAAAAAGGA | TCTTCACCTA | GATCCTTTTA | 3840 |
| AATTAAAAAT | GAAGTTTTAA | ATCAATCTAA | AGTATATATG | AGTAAACTTG | GTCTGACAGT | 3900 |
| TACCAATGCT | TAATCAGTGA | GGCACCTATC | TCAGCGATCT | GTCTATTTCG | TTCATCCATA | 3960 |
| GTTGCCTGAC | TCCCCGTCGT | GTAGATAACT | ACGATACGGG | AGGGCTTACC | ATCTGGCCCC | 4020 |
| AGTGCTGCAA | TGATACCGCG | AGACCCACGC | TCACCGGCTC | CAGATTTATC | AGCAATAAAC | 4080 |
| CAGCCAGCCG | GAAGGGCCGA | GCGCAGAAGT | GGTCCTGCAA | CTTTATCCGC | CTCCATCCAG | 4140 |
| TCTATTAATT | GTTGCCGGGA | AGCTAGAGTA | AGTAGTTCGC | CAGTTAATAG | TTTGCGCAAC | 4200 |
| GTTGTTGCCA | TTGCTACAGG | CATCGTGGTG | TCACGCTCGT | CGTTTGGTAT | GGCTTCATTC | 4260 |

| | | | | | |
|---|---|---|---|---|---|
| AGCTCCGGTT | CCCAACGATC | AAGGCGAGTT | ACATGATCCC | CCATGTTGTG | CAAAAAAGCG | 4320
| GTTAGCTCCT | TCGGTCCTCC | GATCGTTGTC | AGAAGTAAGT | TGGCCGCAGT | GTTATCACTC | 4380
| ATGGTTATGG | CAGCACTGCA | TAATTCTCTT | ACTGTCATGC | CATCCGTAAG | ATGCTTTTCT | 4440
| GTGACTGGTG | AGTACTCAAC | CAAGTCATTC | TGAGAATAGT | GTATGCGGCG | ACCGAGTTGC | 4500
| TCTTGCCCGG | CGTCAATACG | GGATAATACC | GCGCCACATA | GCAGAACTTT | AAAAGTGCTC | 4560
| ATCATTGGAA | AACGTTCTTC | GGGGCGAAAA | CTCTCAAGGA | TCTTACCGCT | GTTGAGATCC | 4620
| AGTTCGATGT | AACCCACTCG | TGCACCCAAC | TGATCTTCAG | CATCTTTTAC | TTTCACCAGC | 4680
| GTTTCTGGGT | GAGCAAAAAC | AGGAAGGCAA | AATGCCGCAA | AAAGGGAAT | AAGGGCGACA | 4740
| CGGAAATGTT | GAATACTCAT | ACTCTTCCTT | TTTCAATATT | ATTGAAGCAT | TTATCAGGGT | 4800
| TATTGTCTCA | TGAGCGGATA | CATATTTGAA | TGTATTTAGA | AAATAAACAA | ATAGGGGTTC | 4860
| CGCGCACATT | TCCCCGAAAA | GTGCCACCTG | ACGTCA | | | 4896

( 2 ) INFORMATION FOR SEQ ID NO:3:

( i ) SEQUENCE CHARACTERISTICS:
        ( A ) LENGTH: 3544 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: EcoRI-HindIII region of plasmid pTS200

( i x ) FEATURE:
        ( A ) NAME/KEY: -
        ( B ) LOCATION: 3227..3504
        ( D ) OTHER INFORMATION: /label=3'nos
            / note= "3'regulatory sequence containing the
            polyadenylation signal of the nopaline synthase
            gene of Agrobacterium T-DNA"

( i x ) FEATURE:
        ( A ) NAME/KEY: -
        ( B ) LOCATION: 2675..3226
        ( D ) OTHER INFORMATION: /label=bar
            / note= "coding region of bar gene of Streptomyces
            hygroscopicus"

( i x ) FEATURE:
        ( A ) NAME/KEY: -
        ( B ) LOCATION: 1841..2674
        ( D ) OTHER INFORMATION: /label=P35S
            / note= "35S promoter of Cauliflower Mosaic Virus"

( i x ) FEATURE:
        ( A ) NAME/KEY: -
        ( B ) LOCATION: complement (626..1803)
        ( D ) OTHER INFORMATION: /label=PCA55
            / note= "promoter of CA55 gene of Zea mays"

( i x ) FEATURE:
        ( A ) NAME/KEY: -
        ( B ) LOCATION: complement (353..625)
        ( D ) OTHER INFORMATION: /label=barstar
            / note= "coding region of barstar gene of Bacillus
            amyloliquefaciens"

( i x ) FEATURE:
        ( A ) NAME/KEY: -
        ( B ) LOCATION: complement (30..352)
        ( D ) OTHER INFORMATION: /label=3'nos
            / note= "3'regulatory sequence containing the
            polyadenylation signal of the nopaline synthase
            gene of Agrobacterium T-DNA"

( i x ) FEATURE:
        ( A ) NAME/KEY: -

(B) LOCATION: 1..6
(D) OTHER INFORMATION: /label=EcoRI (ix) FEATURE:
(A) NAME/KEY: -
(B) LOCATION: 3539..3544
(D) OTHER INFORMATION: /label=HindIII (xi) SEQUENCE DESCRIPTION: SEQ ID NO:3:

| | | | | | | |
|---|---|---|---|---|---|---|
| GAATTCGAGC | TCGGTACCCG | GGGATCTTCC | CGATCTAGTA | ACATAGATGA | CACCGCGCGC | 60 |
| GATAATTTAT | CCTAGTTTGC | GCGCTATATT | TTGTTTTCTA | TCGCGTATTA | AATGTATAAT | 120 |
| TGCGGGACTC | TAATCATAAA | AACCCATCTC | ATAAATAACG | TCATGCATTA | CATGTTAATT | 180 |
| ATTACATGCT | TAACGTAATT | CAACAGAAAT | TATATGATAA | TCATCGCAAG | ACCGGCAACA | 240 |
| GGATTCAATC | TTAAGAAACT | TTATTGCCAA | ATGTTTGAAC | GATCTGCTTC | GGATCCTCTA | 300 |
| GACCAAGCTT | GCGGGTTTGT | GTTTCCATAT | TGTTCATCTC | CCATTGATCG | TATTAAGAAA | 360 |
| GTATGATGGT | GATGTCGCAG | CCTTCCGCTT | TCGCTTCACG | GAAAACCTGA | AGCACACTCT | 420 |
| CGGCGCCATT | TTCAGTCAGC | TGCTTGCTTT | GTTCAAACTG | CCTCCATTCC | AAAACGAGCG | 480 |
| GGTACTCCAC | CCATCCGGTC | AGAGAATCCC | ATAAAGCGTC | CAGGTTTTCA | CCGTAGTATT | 540 |
| CCGGAAGGGC | AAGCTCCTTT | TTCAATGTCT | GGTGGAGGTC | GCTGATACTT | CTGATTTGTT | 600 |
| CCCCGTTAAT | GACTGCTTTT | TTCATGGCTG | CAGCTAGTTA | GCTCGATGTA | TCTTCTGTAT | 660 |
| ATGCAGTGCA | GCTTCTGCGT | TTTGGCTGCT | TTGAGCTGTG | AAATCTCGCT | TTCCAGTCCC | 720 |
| TGCGTGTTTT | ATAGTGCTGT | ACGTTCGTGA | TCGTGAGCAA | ACAGGGCGTG | CCTCAACTAC | 780 |
| TGGTTTGGTT | GGGTGACAGG | CGCCAACTAC | GTGCTCGTAA | CCGATCGAGT | GAGCGTAATG | 840 |
| CAACATTTTT | TCTTCTTCTC | TCGCATTGGT | TTCATCCAGC | CAGGAGACCC | GAATCGAATT | 900 |
| GAAATCACAA | ATCTGAGGTA | CAGTATTTTT | ACAGTACCGT | TCGTTCGAAG | GTCTTCGACA | 960 |
| GGTCAAGGTA | ACAAAATCAG | TTTTAAATTG | TTGTTTCAGA | TCAAAGAAAA | TTGAGATGAT | 1020 |
| CTGAAGGACT | TGGACCTTCG | TCCAATGAAA | CACTTGGACT | AATTAGAGGT | GAATTGAAAG | 1080 |
| CAAGCAGATG | CAACCGAAGG | TGGTGAAAGT | GGAGTTTCAG | CATTGACGAC | GAAAACCTTC | 1140 |
| GAACGGTATA | AAAAGAAGC | CGCAATTAAA | CGAAGATTTG | CCAAAAGAT | GCATCAACCA | 1200 |
| AGGGAAGACG | TGCATACATG | TTTGATGAAA | ACTCGTAAAA | ACTGAAGTAC | GATTCCCCAT | 1260 |
| TCCCCTCCTT | TTCTCGTTTC | TTTTAACTGA | AGCAAAGAAT | TTGTATGTAT | TCCCTCCATT | 1320 |
| CCATATTCTA | GGAGGTTTTG | GCTTTTCATA | CCCTCCTCCA | TTTCAAATTA | TTTGTCATAC | 1380 |
| ATTGAAGATA | TACACCATTC | TAATTTATAC | TAAATTACAG | CTTTTAGATA | CATATATTTT | 1440 |
| ATTATACACT | TAGATACGTA | TTATATAAAA | CACCTAATTT | AAAATAAAAA | ATTATATAAA | 1500 |
| AAGTGTATCT | AAAAAATCAA | AATACGACAT | AATTTGAAAC | GGAGGGGTAC | TACTTATGCA | 1560 |
| AACCAATCGT | GGTAACCCTA | AACCCTATAT | GAATGAGGCC | ATGATTGTAA | TGCACCGTCT | 1620 |
| GATTAACCAA | GATATCAATG | GTCAAAGATA | TACATGATAC | ATCCAAGTCA | CAGCGAAGGC | 1680 |
| AAATGTGACA | ACAGTTTTTT | TTACCAGAGG | GACAAGGGAG | AATATCTATT | CAGATGTCAA | 1740 |
| GTTCCCGTAT | CACACTGCCA | GGTCCTTACT | CCAGACCATC | TTCCGGCTCT | ATTGATGCAT | 1800 |
| ACCAGGAATT | GATCTAGAGT | CGACCTGCAG | GCATGCAAGC | TCCTACGCAG | CAGGTCTCAT | 1860 |
| CAAGACGATC | TACCCGAGTA | ACAATCTCCA | GGAGATCAAA | TACCTTCCCA | AGAAGGTTAA | 1920 |
| AGATGCAGTC | AAAAGATTCA | GGACTAATTG | CATCAAGAAC | ACAGAGAAAG | ACATATTTCT | 1980 |
| CAAGATCAGA | AGTACTATTC | CAGTATGGAC | GATTCAAGGC | TTGCTTCATA | AACCAAGGCA | 2040 |
| AGTAATAGAG | ATTGGAGTCT | CTAAAAAGGT | AGTTCCTACT | GAATCTAAGG | CCATGCATGG | 2100 |

-continued

| | | | | | | |
|---|---|---|---|---|---|---|
| AGTCTAAGAT | TCAAATCGAG | GATCTAACAG | AACTCGCCGT | GAAGACTGGC | GAACAGTTCA | 2160 |
| TACAGAGTCT | TTTACGACTC | AATGACAAGA | AGAAAATCTT | CGTCAACATG | GTGGAGCACG | 2220 |
| ACACTCTGGT | CTACTCCAAA | AATGTCAAAG | ATACAGTCTC | AGAAGACCAA | AGGGCTATTG | 2280 |
| AGACTTTTCA | ACAAAGGATA | ATTTCGGGAA | ACCTCCTCGG | ATTCCATTGC | CCAGCTATCT | 2340 |
| GTCACTTCAT | CGAAAGGACA | GTAGAAAAGG | AAGGTGGCTC | CTACAAATGC | CATCATTGCG | 2400 |
| ATAAAGGAAA | GGCTATCATT | CAAGATGCCT | CTGCCGACAG | TGGTCCCAAA | GATGGACCCC | 2460 |
| CACCCACGAG | GAGCATCGTG | GAAAAAGAAG | ACGTTCCAAC | CACGTCTTCA | AAGCAAGTGG | 2520 |
| ATTGATGTGA | CATCTCCACT | GACGTAAGGG | ATGACGCACA | ATCCACTAT | CCTTCGCAAG | 2580 |
| ACCCTTCCTC | TATATAAGGA | AGTTCATTTC | ATTTGGAGAG | GACACGCTGA | AATCACCAGT | 2640 |
| CTCTCTCTAT | AAATCTATCT | CTCTCTCTAT | AACCATGGAC | CCAGAACGAC | GCCCGGCCGA | 2700 |
| CATCCGCCGT | GCCACCGAGG | CGGACATGCC | GGCGGTCTGC | ACCATCGTCA | ACCACTACAT | 2760 |
| CGAGACAAGC | ACGGTCAACT | TCCGTACCGA | GCCGCAGGAA | CCGCAGGAGT | GGACGGACGA | 2820 |
| CCTCGTCCGT | CTGCGGGAGC | GCTATCCCTG | GCTCGTCGCC | GAGGTGGACG | GCGAGGTCGC | 2880 |
| CGGCATCGCC | TACGCGGGCC | CCTGGAAGGC | ACGCAACGCC | TACGACTGGA | CGGCCGAGTC | 2940 |
| GACCGTGTAC | GTCTCCCCCC | GCCACCAGCG | GACGGGACTG | GGCTCCACGC | TCTACACCCA | 3000 |
| CCTGCTGAAG | TCCCTGGAGG | CACAGGGCTT | CAAGAGCGTG | GTCGCTGTCA | TCGGGCTGCC | 3060 |
| CAACGACCCG | AGCGTGCGCA | TGCACGAGGC | GCTCGGATAT | GCCCCCGCG | GCATGCTGCG | 3120 |
| GGCGGCCGGC | TTCAAGCACG | GGAACTGGCA | TGACGTGGGT | TTCTGGCAGC | TGGACTTCAG | 3180 |
| CCTGCCGGTA | CCGCCCCGTC | CGGTCCTGCC | CGTCACCGAG | ATCTGATCTC | ACGCGTCTAG | 3240 |
| GATCCGAAGC | AGATCGTTCA | AACATTTGGC | AATAAAGTTT | CTTAAGATTG | AATCCTGTTG | 3300 |
| CCGGTCTTGC | GATGATTATC | ATATAATTTC | TGTTGAATTA | CGTTAAGCAT | GTAATAATTA | 3360 |
| ACATGTAATG | CATGACGTTA | TTTATGAGAT | GGGTTTTTAT | GATTAGAGTC | CCGCAATTAT | 3420 |
| ACATTTAATA | CGCGATAGAA | AACAAATAT | AGCGCGCAAA | CTAGGATAAA | TTATCGCGCG | 3480 |
| CGGTGTCATC | TATGTTACTA | GATCGGGAAG | ATCCTCTAGA | GTCGACCTGC | AGGCATGCAA | 3540 |
| GCTT | | | | | | 3544 |

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: oligonucleotide 1

( x i ) SEQUENCE DESCRIPTION: SEQ ID NO:4:

CGTTTCTCGA ATCCGACGAG G        21

( 2 ) INFORMATION FOR SEQ ID NO:5:

( i ) SEQUENCE CHARACTERISTICS:
        ( A ) LENGTH: 4824 base pairs
        ( B ) TYPE: nucleic acid
        ( C ) STRANDEDNESS: double
        ( D ) TOPOLOGY: circular ( i i ) MOLECULE TYPE: DNA (genomic)

( v i ) ORIGINAL SOURCE:

(A) ORGANISM: plasmid pCOL9

(ix) FEATURE:
  (A) NAME/KEY: -
  (B) LOCATION: 396..401
  (D) OTHER INFORMATION: /label=EcoRI (ix) FEATURE:
  (A) NAME/KEY: -
  (B) LOCATION: 2367..2379
  (D) OTHER INFORMATION: /label=SfiI (ix) FEATURE:
  (A) NAME/KEY: -
  (B) LOCATION: 884..888
  (D) OTHER INFORMATION: /label= C1- S
    / note= "TGCAG (in C1) which in C1-S allele is replaced with TTAGG"

(xi) SEQUENCE DESCRIPTION: SEQ ID NO:5:

| | | | | | |
|---|---|---|---|---|---|
| TCGCGCGTTT | CGGTGATGAC | GGTGAAAACC | TCTGACACAT | GCAGCTCCCG | GAGACGGTCA | 60 |
| CAGCTTGTCT | GTAAGCGGAT | GCCGGGAGCA | GACAAGCCCG | TCAGGGCGCG | TCAGCGGGTG | 120 |
| TTGGCGGGTG | TCGGGGCTGG | CTTAACTATG | CGGCATCAGA | GCAGATTGTA | CTGAGAGTGC | 180 |
| ACCATATGCG | GTGTGAAATA | CCGCACAGAT | GCGTAAGGAG | AAAATACCGC | ATCAGGCGCC | 240 |
| ATTCGCCATT | CAGGCTGCGC | AACTGTTGGG | AAGGGCGATC | GGTGCGGGCC | TCTTCGCTAT | 300 |
| TACGCCAGCT | GGCGAAAGGG | GGATGTGCTG | CAAGGCGATT | AAGTTGGGTA | ACGCCAGGGT | 360 |
| TTTCCCAGTC | ACGACGTTGT | AAAACGACGG | CCAGTGAATT | CGCTTACGGT | CTCAAACAAG | 420 |
| CAATTTACAC | TCAGTTGGTT | GTAATATGTG | GACAATAAAA | CTACAAACTA | GACACAAATC | 480 |
| ATACCATAGA | CGGAGTGGTA | GCAGAGGGTA | CGCGCGAGGG | TGAGATAGAG | GATTCTCCTA | 540 |
| AAATAAATGC | ACTTTAGATG | GGTAGGGTGG | GGTGAGGCCT | CTCCTAAAAT | GAAACTCGTT | 600 |
| TAATGTTTCT | AAAAATAGTT | TTCACTGGTG | ATCCTTAGTT | ACTGGCATGT | AAAAATGATG | 660 |
| ATTTCTACTG | TCTCTCATAT | GGACGGTTAT | AAAAAATACC | ATTATATTGA | AATAGGTCT | 720 |
| CTGCTGCTAC | ACTCGCCCTC | ATAGCAGATC | ATGCATGCAC | GCATCATTCG | ATCAGTTTTC | 780 |
| GTTCTGATGC | AGTTTTCGAT | AAATGCCAAT | TTTTTAACTG | CATACGTTGC | CCTTGCTCAG | 840 |
| CACCAGCACA | GCAGTGTCGT | GTCGTCCATG | CATGCACTTT | AGGTGCAGTG | CAGGGCCTCA | 900 |
| ACTCGGCCAC | GTAGTTAGCG | CCACTGCTAC | AGATCGAGGC | ACCGGTCAGC | CGGCCACGCA | 960 |
| CGTCGACCGC | GCGCGTGCAT | TTAAATACGC | CGACGACGGA | GCTTGATCGA | CGAGAGAGCG | 1020 |
| AGCGCGATGG | GGAGGAGGGC | GTGTTGCGCG | AAGGAAGGCG | TTAAGAGAGG | GGCGTGGACG | 1080 |
| AGCAAGGAGG | ACGATGCCTT | GGCCGCCTAC | GTCAAGGCCC | ATGGCGAAGG | CAAATGGAGG | 1140 |
| GAAGTGCCCC | AGAAAGCCGG | TAAAACTAGC | TAGTCTTTTT | ATTTCATTTT | GGGATCATAT | 1200 |
| ATATACCCCC | GAGGCAAGAC | CGGAGGACGA | TCACGTGTGT | GGGTGCAGGT | TTGCGTCGGT | 1260 |
| GCGGCAAGAG | CTGCCGGCTG | CGGTGGCTGA | ACTACCTCCG | GCCCAACATC | AGGCGCGGCA | 1320 |
| ACATCTCCTA | CGACGAGGAG | GATCTCATCA | TCCGCCTCCA | CAGGCTCCTC | GGCAACAGGT | 1380 |
| CTGTGCAGTG | GCCAGTGGTG | GGCTAGCTTA | TTACACGAGC | TGACGACGAG | GCGATCGATC | 1440 |
| GAGCGTCTGC | TGCGAATTCA | TCTGTTCCGG | TGTCGGCCGT | GTGAGAGTGA | GCTCATTCAT | 1500 |
| ATGTACATGC | GTGTTGGCGC | GCAGGTGGTC | GCTGATTGCA | GGCAGGCTGC | CTGGCCGAAC | 1560 |
| AGACAATGAA | ATCAAGAACT | ACTGGAACAG | CACGCTGGGC | CGGAGGGCAG | GCGCCGGCGC | 1620 |
| CGGCGCCGGC | GGCAGCTGGG | TCGTCGTCGC | GCCGGACACC | GGCTCGACG | CCACCCCGGC | 1680 |
| CGCGACGTCG | GGCGCCTGCG | AGACCGGCCA | GAATAGCGCC | GCTCATCGCG | CGGACCCCGA | 1740 |
| CTCAGCCGGG | ACGACGACGA | CCTCGGCGGC | GGCGGTGTGG | GCGCCCAAGG | CCGTGCGGTG | 1800 |

```
CACGGGCGGA CTCTTCTTCT TCCACCGGGA CACGACGCCG GCGCACGCGG GCGAGACGGC   1860
GACGCCAATG GCCGGTGGAG GTGGAGGAGG AGGAGGAGAA GCAGGGTCGT CGGACGACTG   1920
CAGCTCGGCG GCGTCGGTAT CGCTTCGCGT CGGAAGCCAC GACGAGCCGT GCTTCTCCGG   1980
CGACGGTGAC GGCGACTGGA TGGACGACGT GAGGGCCCTG GCGTCGTTTC TCGAGTCCGA   2040
CGAGGACTGG CTCCGCTGTC AGACGGCCGG GCAGCTTGCG TAGACAACAA GTACACGTAT   2100
AGATGTCCAA TAAGCACGAG GCCCGCGAGC CCGGCACGAA GCCCGCTTTT TGGGCCCGGT   2160
CCGAGCCCGG CACGGCCCGG TTATATGCAG ACCCGGGCCG GCCCGGCACG AATAAGCGGG   2220
CCGGGCTCGG ACAGGAAATT AGGCACGGTG AGCTAGCCCG GCACGGCCCG TTTAGGTCTA   2280
AGCCCGTTAA GCCCGTTTTT TTACACTAAA ACGTGCTTCT CGGCCCGCAT AGCCCGCTTC   2340
TCGGCCCGCT TTTTCGTGC TAAACGGGCC GGCCCGGCCC GGTTTAGGCC CGTTGCGGGC   2400
CGGGCTCGGA CAGGAAATTG AGCCCGCGTG CTTAGCCGGC CCGGCCCGGT TTTTAATCG   2460
TGCCTGGCGG GCCAGGCCCA AAACGGGCCG GGCTTCACCG GGCCCGGGCC GGACCGGGCC   2520
GGGCGGCCCG TTTGGACATC TCTAAGTACA CGTATGGAGG AGAATATATA TATAGTCATG   2580
CGTACAGCTT GGCGTAATCA TGGTCATAGC TGTTTCCTGT GTGAAATTGT TATCCGCTCA   2640
CAATTCCACA CAACATACGA GCCGGAAGCA TAAAGTGTAA AGCCTGGGGT GCCTAATGAG   2700
TGAGCTAACT CACATTAATT GCGTTGCGCT CACTGCCCGC TTTCCAGTCG GGAAACCTGT   2760
CGTGCCAGCT GCATTAATGA ATCGGCCAAC GCGCGGGGAG AGGCGGTTTG CGTATTGGGC   2820
GCTCTTCCGC TTCCTCGCTC ACTGACTCGC TGCGCTCGGT CGTTCGGCTG CGGCGAGCGG   2880
TATCAGCTCA CTCAAAGGCG GTAATACGGT TATCCACAGA ATCAGGGGAT AACGCAGGAA   2940
AGAACATGTG AGCAAAAGGC CAGCAAAAGG CCAGGAACCG TAAAAAGGCC GCGTTGCTGG   3000
CGTTTTTCCA TAGGCTCCGC CCCCCTGACG AGCATCACAA AAATCGACGC TCAAGTCAGA   3060
GGTGGCGAAA CCCGACAGGA CTATAAAGAT ACCAGGCGTT TCCCCCTGGA AGCTCCCTCG   3120
TGCGCTCTCC TGTTCCGACC CTGCCGCTTA CCGGATACCT GTCCGCCTTT CTCCCTTCGG   3180
GAAGCGTGGC GCTTTCTCAA TGCTCACGCT GTAGGTATCT CAGTTCGGTG TAGGTCGTTC   3240
GCTCCAAGCT GGGCTGTGTG CACGAACCCC CCGTTCAGCC CGACCGCTGC GCCTTATCCG   3300
GTAACTATCG TCTTGAGTCC AACCCGGTAA GACACGACTT ATCGCCACTG GCAGCAGCCA   3360
CTGGTAACAG GATTAGCAGA GCGAGGTATG TAGGCGGTGC TACAGAGTTC TTGAAGTGGT   3420
GGCCTAACTA CGGCTACACT AGAAGGACAG TATTTGGTAT CTGCGCTCTG CTGAAGCCAG   3480
TTACCTTCGG AAAAAGAGTT GGTAGCTCTT GATCCGGCAA ACAAACCACC GCTGGTAGCG   3540
GTGGTTTTTT TGTTTGCAAG CAGCAGATTA CGCGCAGAAA AAAAGGATCT CAAGAAGATC   3600
CTTTGATCTT TTCTACGGGG TCTGACGCTC AGTGGAACGA AAACTCACGT TAAGGGATTT   3660
TGGTCATGAG ATTATCAAAA AGGATCTTCA CCTAGATCCT TTTAAATTAA AAATGAAGTT   3720
TTAAATCAAT CTAAAGTATA TATGAGTAAA CTTGGTCTGA CAGTTACCAA TGCTTAATCA   3780
GTGAGGCACC TATCTCAGCG ATCTGTCTAT TTCGTTCATC CATAGTTGCC TGACTCCCCG   3840
TCGTGTAGAT AACTACGATA CGGGAGGGCT TACCATCTGG CCCCAGTGCT GCAATGATAC   3900
CGCGAGACCC ACGCTCACCG GCTCCAGATT TATCAGCAAT AAACCAGCCA GCCGGAAGGG   3960
CCGAGCGCAG AAGTGGTCCT GCAACTTTAT CCGCCTCCAT CCAGTCTATT AATTGTTGCC   4020
GGGAAGCTAG AGTAAGTAGT TCGCCAGTTA ATAGTTTGCG CAACGTTGTT GCCATTGCTA   4080
CAGGCATCGT GGTGTCACGC TCGTCGTTTG GTATGGCTTC ATTCAGCTCC GGTTCCCAAC   4140
GATCAAGGCG AGTTACATGA TCCCCCATGT TGTGCAAAAA AGCGGTTAGC TCCTTCGGTC   4200
```

-continued

| | | | | | |
|---|---|---|---|---|---|
|CTCCGATCGT|TGTCAGAAGT|AAGTTGGCCG|CAGTGTTATC|ACTCATGGTT|ATGGCAGCAC|4260|
|TGCATAATTC|TCTTACTGTC|ATGCCATCCG|TAAGATGCTT|TTCTGTGACT|GGTGAGTACT|4320|
|CAACCAAGTC|ATTCTGAGAA|TAGTGTATGC|GGCGACCGAG|TTGCTCTTGC|CCGGCGTCAA|4380|
|TACGGGATAA|TACCGCGCCA|CATAGCAGAA|CTTTAAAAGT|GCTCATCATT|GGAAAACGTT|4440|
|CTTCGGGGCG|AAAACTCTCA|AGGATCTTAC|CGCTGTTGAG|ATCCAGTTCG|ATGTAACCCA|4500|
|CTCGTGCACC|CAACTGATCT|TCAGCATCTT|TTACTTTCAC|CAGCGTTTCT|GGGTGAGCAA|4560|
|AAACAGGAAG|GCAAAATGCC|GCAAAAAAGG|GAATAAGGGC|GACACGGAAA|TGTTGAATAC|4620|
|TCATACTCTT|CCTTTTTCAA|TATTATTGAA|GCATTTATCA|GGGTTATTGT|CTCATGAGCG|4680|
|GATACATATT|TGAATGTATT|TAGAAAAATA|AACAAATAGG|GGTTCCGCGC|ACATTTCCCC|4740|
|GAAAAGTGCC|ACCTGACGTC|TAAGAAACCA|TTATTATCAT|GACATTAACC|TATAAAAATA|4800|
|GGCGTATCAC|GAGGCCCTTT|CGTC| | | |4824|

( 2 ) INFORMATION FOR SEQ ID NO:6:

( i ) SEQUENCE CHARACTERISTICS:
        ( A ) LENGTH: 3915 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: EcoRI-Hind III region of plasmid pCOL13

( i x ) FEATURE:
        ( A ) NAME/KEY: prim_transcript
        ( B ) LOCATION: 188

( i x ) FEATURE:
        ( A ) NAME/KEY: exon
        ( B ) LOCATION: 188..212

( i x ) FEATURE:
        ( A ) NAME/KEY: intron
        ( B ) LOCATION: 213..556

( i x ) FEATURE:
        ( A ) NAME/KEY: exon
        ( B ) LOCATION: 557..718

( i x ) FEATURE:
        ( A ) NAME/KEY: intron
        ( B ) LOCATION: 719..1224

( i x ) FEATURE:
        ( A ) NAME/KEY: exon
        ( B ) LOCATION: 1225..2770
        ( D ) OTHER INFORMATION: /codon_start= 2
            / note= "exon containing 3'end coding region of
            B-peru gene"

( i x ) FEATURE:
        ( A ) NAME/KEY: CDS
        ( B ) LOCATION: 576..718

( i x ) FEATURE:
        ( A ) NAME/KEY: CDS
        ( B ) LOCATION: 1225..2770

( i x ) FEATURE:
        ( A ) NAME/KEY: -
        ( B ) LOCATION: 1268..2770
        ( D ) OTHER INFORMATION: /note= "3'end of B-peru coding
            region which is derived from cDNA"

( i x ) FEATURE:
        ( A ) NAME/KEY: 3'UTR ( B ) LOCATION: 2771..3272

( i x ) FEATURE:
                ( A ) NAME/KEY: -
                ( B ) LOCATION: 3273..3891
                ( D ) OTHER INFORMATION: /label=3'region
                        / note= "further 3'flanking region of B-peru gene.
                        This region is only of approximate length and the
                        sequence needs to be confirmed."

( i x ) FEATURE:
                ( A ) NAME/KEY: -
                ( B ) LOCATION: 1..6
                ( D ) OTHER INFORMATION: /label=EcoRI ( i x ) FEATURE:
                ( A ) NAME/KEY: -
                ( B ) LOCATION: 11..16
                ( D ) OTHER INFORMATION: /label=XbaI ( i x ) FEATURE:
                ( A ) NAME/KEY: -
                ( B ) LOCATION: 45..50
                ( D ) OTHER INFORMATION: /label=KpnI ( i x ) FEATURE:
                ( A ) NAME/KEY: -
                ( B ) LOCATION: 265..270
                ( D ) OTHER INFORMATION: /label=HindIII ( i x ) FEATURE:
                ( A ) NAME/KEY: -
                ( B ) LOCATION: 329..334
                ( D ) OTHER INFORMATION: /label=XbaI ( i x ) FEATURE:
                ( A ) NAME/KEY: -
                ( B ) LOCATION: 835..840
                ( D ) OTHER INFORMATION: /label=BamHI ( i x ) FEATURE:
                ( A ) NAME/KEY: -
                ( B ) LOCATION: 1268..1273
                ( D ) OTHER INFORMATION: /label=MluI ( i x ) FEATURE:
                ( A ) NAME/KEY: -
                ( B ) LOCATION: 2787..2792
                ( D ) OTHER INFORMATION: /label=HindIII ( i x ) FEATURE:
                ( A ) NAME/KEY: -
                ( B ) LOCATION: 2883..2888
                ( D ) OTHER INFORMATION: /label=MunI ( i x ) FEATURE:
                ( A ) NAME/KEY: -
                ( B ) LOCATION: 2827..2832
                ( D ) OTHER INFORMATION: /label=HindIII ( i x ) FEATURE:
                ( A ) NAME/KEY: -
                ( B ) LOCATION: 3892..3897
                ( D ) OTHER INFORMATION: /label=SalI ( i x ) FEATURE:
                ( A ) NAME/KEY: -
                ( B ) LOCATION: 3910..3915
                ( D ) OTHER INFORMATION: /label=HindIII ( i x ) FEATURE:
                ( A ) NAME/KEY: -
                ( B ) LOCATION: 3892..3915
                ( D ) OTHER INFORMATION: /label=polylinker
                        / note= "part of polylinker of pUC19"

( x i ) SEQUENCE DESCRIPTION: SEQ ID NO:6:

GAATTCAGGT    TCTAGACTAT    TCTTGTGGCC    TCGGGCGGAT    GGCGGGTACC    CATGTCTTCG                60

-continued

| | | | | | |
|---|---|---|---|---|---|
| TTAGGCTTAT | CTGACCGTGG | AGATGAAATC | TAACGGCTCA | TAGAAATTAA | ACTAACGTGG | 120
| ACACTCTGTC | CTTGCTGTTT | TGCTCCCTGC | TCTTTATATA | TAGAATGCCT | GCTTGCATTG | 180
| CACCCGTACG | TACAGCGTAG | CGCGGAGTGG | AGGTGAGCTC | CTCCTCCGAT | TCTTGCCTAA | 240
| TCTTTGGTCT | TTGCACACGT | ACGAAAGCTT | TTTGCATTGT | TTCGTTGCTT | CTGGATGATC | 300
| AGTACTCTTA | GATATTAAGC | GATACCGATC | TAGAATCGAG | TTGTTGTACT | CTCTCTGTCC | 360
| CTTTTGTGCA | GCTATAACTA | GCTAGGTTCC | TTCGCATAGA | GCCTCTCTAC | AGAGTACAGA | 420
| CTAGCTAGCA | GTGTCAGACA | CGAAATGGAA | ATGGTCACTT | CCAAATTGCA | CGAGCTGGAA | 480
| TTATATACTC | TTCTGATCTT | CTTCACCGTC | TCTTTATAGC | GTGATATGCG | TTTCTGGCTT | 540
| CTTGCTTACG | TGAAGGATTA | TTAGTAAGGC | GCGTGATGGC | GCTCTCAGCT | TCCCCGGCTC | 600
| AGGAAGAACT | GCTGCAGCCT | GCTGGGAGGC | CGTTGAGGAA | GCAGCTTGCT | GCAGCCGCGA | 660
| GGAGCATCAA | CTGGAGCTAT | GCCCTCTTCT | GGTCCATTTC | AAGCACTCAA | CGACCTCGGT | 720
| AAATGGAAGT | CCTGATAATC | TATAATTTGT | CTGGCAGTTT | TCTACAACTC | TGGTGAATGA | 780
| TCGTCACTTC | GTTTGCCTGA | TACATACATA | CATACATATG | AATAAAGAA | AGTCGGATCC | 840
| CGTGATGCGA | TTGTAGTTAT | CGCTTTTCCG | CAAAATGGTT | GCTTTTGAA | TCTGCATTCG | 900
| TTTTTTTCCC | ACATCTTCTT | CCTTCTCGCG | AGTAACGACA | ACGCCACCCG | CGCCGCCTGC | 960
| CGCCCATCGC | CCCGCCTTGG | CCGGCGAGAG | CCTCAGCCTA | TTACACCAGC | GGCGACCTCT | 1020
| TTTCCCCTTC | CTCTCACCGC | CCTCGTGGCC | GTGCTCTCCC | CCGCTCTAAC | CTGGTCTGGC | 1080
| CGCCTCCGCT | GCCACCTGCT | CCGGCGGCCT | CACCCGCGTC | TTTCTCGTCC | CTACCCTCTC | 1140
| TGCCTCTGGG | CGCATCATCA | TCTGATATTC | TGATGCAAAT | AAAAAAGGTA | TACCATATAA | 1200
| GGACAACAGA | AAATATGGTT | GCAGGGTGCT | GACGTGGACG | GACGGGTTCT | ACAATGGCGA | 1260
| GGTGAAGACG | CGTAAGATCT | CCCACTCCGT | GGAGCTGACA | GCCGACCAGC | TGCTCATGCA | 1320
| GAGGAGCGAG | CAGCTCCGGG | AGCTCTACGA | GGCCCTCCGG | TCCGGCGAGT | GCGACCGCCG | 1380
| CGGCGCGCGG | CCGGTGGGCT | CGCTGTCGCC | GGAGGACCTC | GGGGACACCG | AGTGGTACTA | 1440
| CGTGATCTGC | ATGACCTACG | CCTTCCTGCC | GGGCCAAGGC | TTGCCCGGCA | GGAGTTCCGC | 1500
| GAGCAACGAG | CATGTCTGGC | TGTGCAACGC | GCACCTCGCC | GGCAGCAAGG | ACTTCCCCCG | 1560
| CGCGCTCCTG | GCCAAGAGCG | CGTCCATTCA | GACAATCGTC | TGCATCCCGC | TCATGGGTGG | 1620
| CGTGCTTGAG | CTTGGTACTA | CTGATAAGGT | GCCGGAGGAC | CCGGACTTGG | TCAGCCGAGC | 1680
| AACCGTAGCA | TTCTGGGAGC | CGCAATGTCC | GACATACTCG | AAAGAGCCGA | GCTCCAACCC | 1740
| GTCAGCATAC | GAAACCGGGG | AAGCCGCATA | CATAGTCGTG | TTGGAGGACC | TCGATCACAA | 1800
| TGCCATGGAC | ATGGAGACGG | TGACTGCCGC | CGCCGGGAGA | CACGGAACCG | GACAGGAGCT | 1860
| AGGAGAAGTC | GAGAGCCCGT | CAAATGCAAG | CCTGGAGCAC | ATCACCAAGG | GGATCGACGA | 1920
| GTTCTACAGC | CTCTGCGAGG | AAATGGACGT | GCAGCCGCTA | GAGGATGCCT | GGATAATGGA | 1980
| CGGGTCTAAT | TTCGAAGTCC | CGTCGTCAGC | GCTCCCGGTG | GATGGCTCAA | GCGCACCCGC | 2040
| TGATGGTTCT | CGCGCGACAA | GTTTCGTGGT | TTGGACGAGG | TCATCGCACT | CCTGCTCGGG | 2100
| TGAAGCGGCG | GTGCCGGTCA | TCGAAGAGCC | GCAGAAATTG | CTGAAGAAAG | CGTTGGCCGG | 2160
| CGGCGGTGCT | TGGGCGAACA | CGAACTGCGG | TGGCGGGGGC | ACGACGGTAA | CAGCCCAGGA | 2220
| AAACGGCGCC | AAGAACCACG | TCATGTCAGA | GCGAAAGCGC | CGGGAGAAGC | TCAACGAGAT | 2280
| GTTCCTCGTT | CTCAAGTCGT | TGGTTCCCTC | CATTCACAAG | GTGGACAAAG | CATCCATCCT | 2340
| CGCCGAAACG | ATAGCCTATC | TAAAGGAGCT | TCAACGAAGG | GTACAAGAAC | TGGAATCCAG | 2400
| GAGGCAAGGT | GGCAGTGGGT | GTGTCAGCAA | GAAAGTCTGT | GTGGGCTCCA | ACTCCAAGAG | 2460

-continued

| | | | | | | |
|---|---|---|---|---|---|---|
| GAAGAGCCCA | GAGTTCGCCG | GTGGCGCGAA | GGAGCACCCC | TGGGTCCTCC | CCATGGACGG | 2520 |
| CACCAGCAAC | GTCACCGTCA | CCGTCTCGGA | CACGAACGTG | CTCCTGGAGG | TGCAATGCCG | 2580 |
| GTGGGAGAAG | CTCCTGATGA | CACGGGTGTT | CGACGCCATC | AAGAGCCTCC | ATTTGGACGC | 2640 |
| TCTCTCGGTT | CAGGCTTCGG | CACCAGATGG | CTTCATGAGG | CTCAAGATAG | GAGCTCAGTT | 2700 |
| TGCAGGCTCC | GGCGCCGTCG | TGCCCGGAAT | GATCAGCCAA | TCTCTTCGTA | AAGCTATAGG | 2760 |
| GAAGCGATGA | AAGGGCGCTA | CATGTGAAGC | TTAATTAATG | GAAGCAAACT | TGTATTTCTT | 2820 |
| GTGCAAAAGC | TTACTATATA | TTTCTGCAAA | ACCTGGTGTG | CCTTGTTTTG | ATTTTCAGTC | 2880 |
| GCCAATTGTG | CCTTTGTTTT | TATCAAGTGA | TGATCTACAC | ATATATATAG | GAATATTTGA | 2940 |
| AAAGAGCGAT | GTCATAGGGT | TTTTTTATTA | CAAGGAACAA | GTCTTTCACG | TGCTGGCCTC | 3000 |
| ACAAATCCTA | AGAGAAAATC | TGCTCATTTT | GATTGCGTTC | CGCAACAACT | CTGTAATCCA | 3060 |
| TATCCTATGT | ATCCGATCAA | CTAGTCGATA | GCCTCCGTCC | GCCACATCAT | CATATATCTA | 3120 |
| TCTATGTGTG | TCATCTGACA | CATACTCCTC | GCGTACTGTG | CTGACATATG | ATACTGACAC | 3180 |
| AGCATATATG | CATGCACATC | GTCACACGAC | ATATATCTCG | CTACTACACA | GATATTGGAT | 3240 |
| ACGATACTAT | ATAGCATCAT | GCGTGCTGCG | ATNNNNNNN | NNNNNNNNNN | NNNNNNNNNN | 3300 |
| NNNNNNNNNN | NNNNNNNNNN | NNNNNNNNNN | NNNNNNNNNN | NNNNNNNNNN | NNNNNNNNNN | 3360 |
| NNNNNNNNNN | NNNNNNNNNN | NNNNNNNNNN | NNNNNNNNNN | NNNNNNNNNN | NNNNNNNNNN | 3420 |
| NNNNNNNNNN | NNNNNNNNNN | NNNNNNNNNN | NNNNNNNNNN | NNNNNNNNNN | NNNNNNNNNN | 3480 |
| NNNNNNNNNN | NNNNNNNNNN | NNNNNNNNNN | NNNNNNNNNN | NNNNNNNNNN | NNNNNNNNNN | 3540 |
| NNNNNNNNNN | NNNNNNNNNN | NNNNNNNNNN | NNNNNNNNNN | NNNNNNNNNN | NNNNNNNNNN | 3600 |
| NNNNNNNNNN | NNNNNNNNNN | NNNNNNNNNN | NNNNNNNNNN | NNNNNNNNNN | NNNNNNNNNN | 3660 |
| NNNNNNNNNN | NNNNNNNNNN | NNNNNNNNNN | NNNNNNNNNN | NNNNNNNNNN | NNNNNNNNNN | 3720 |
| NNNNNNNNNN | NNNNNNNNNN | NNNNNNNNNN | NNNNNNNNNN | NNNNNNNNNN | NNNNNNNNNN | 3780 |
| NNNNNNNNNN | NNNNNNNNNN | NNNNNNNNNN | NNNNNNNNNN | NNNNNNNNNN | NNNNNNNNNN | 3840 |
| NNNNNNNNNN | NNNNNNNNNN | NNNNNNNNNN | NNNNNNNNNN | NNNNNNNNNN | NGTCGACCTG | 3900 |
| CAGGCATGCA | AGCTT | | | | | 3915 |

What is claimed is:

1. A process for maintaining a male-sterile corn line, said process comprising:

(1) crossing:
  (a) a male-sterile corn line to be maintained comprising male-sterile parent plants which comprise a homozygous male-sterility genotype at a first genetic locus and which do not comprise a functional regulatory gene required for anthocyanin production in corn seeds; with
  (b) a maintainer corn line comprising male-fertile parent plants which comprise said homozygous male-sterility genotype at said first genetic locus, and which further comprise, at a second genetic locus which segregates independently from said first genetic locus, foreign DNA comprising:
    I) a restorer gene the expression of which prevents the phenotypic expression of said homozygous male-sterility genotype; and
    II) at least one gene selected from the group of a first gene that is expressed in corn seeds to produce a first active regulatory protein having the same activity as the protein encoded by a functional R or B gene, and a second gene that is expressed in corn seeds to produce a second active regulatory protein having the same activity as the protein encoded by a functional C1 gene, wherein said foreign DNA is heterozygous at said second genetic locus; wherein said male-sterile plants produce seeds producing anthocyanin, as well as seeds not producing anthocyanin, said anthocyanin being produced only in seeds comprising said at least one gene in said foreign DNA;

2) harvesting seeds from said male-sterile parent plants; and 3) selecting from the harvested seeds, those seeds which do not produce anthocyanin, said selected seeds being capable of growing into a new generation of male-sterile plants.

2. The process of claim 1, in which said at least one gene in said foreign DNA is expressed at least in the aleurone of corn seeds.

3. The process of claim 2, in which said male-sterile parent plants do not contain a gene that is functionally expressed in the aleurone of corn seeds and encodes an active regulatory protein having the same activity as the protein encoded by a functional R or B gene, and wherein said foreign DNA in said male-fertile parent plants comprises said first gene.

4. The process of claim 3, in which said gene comprises a DNA encoding the B-peru protein which is under the control of a promoter of the B-peru gene, a promoter comprising the nucleotide sequence of SEQ ID No. 6 between positions 1 and 188, a 35S promoter, a promoter comprising the sequence of SEQ ID No. 1 between position 447 and 1061 or a promoter comprising the sequence of SEQ ID No. 1 between positions 447 and 1061 in which TGCAG between positions 935 and 939 is changed to TTAGG.

5. The process of claim 4, in which said first gene does not comprise an intron.

6. The process of claim 2, in which said male-sterile parent plants do not contain a gene that is functionally expressed in the aleurone of corn seeds which gene encodes an active regulatory protein having the same activity as a functional C1 gene, and wherein said DNA in said male-fertile parent plants comprises said second gene.

7. The process of claim 6, in which said second gene comprises a DNA encoding the C1 protein which is under the control of a promoter of the B-peru gene, a promoter comprising the nucleotide sequence of SEQ ID No. 6 between positions 1 and 188, a 35S promoter, a promoter comprising the sequence of SEQ ID No. 1 between positions 447 and 1061 or a promoter comprising the sequence of SEQ ID No. 1 between positions 447 and 1061 in which TGCAG between positions 935 and 939 is changed to TTAGG.

8. The process of claim 2, in which said male-sterile parent plants do not contain a gene that is functionally expressed in the aleurone of corn seeds and encodes an active regulatory protein having the same activity as the protein encoded by a functional R or B gene, and do not contain a gene that is functionally expressed in the aleuron of corn seeds and encodes an active regulatory protein having the same activity as the protein encoded by a functional C1 gene, and wherein said foreign DNA is said male-fertile parent plants comprises said first gene and said second gene.

9. The process of claim 8, in which the said first gene comprises a DNA encoding a B-peru protein under the control of a promoter of the B-peru gene, a promoter comprising the nucleotide sequence of SEQ ID No. 6 between positions 1 and 188, a 35S promoter, or a promoter comprising the sequence of SEQ ID No. 1 between positions 447 and 1061 in which TGCAG between positions 935 and 939 is changed to TTAGG; and in which said second gene comprises a DNA encoding the C1 protein under the control of a promoter of the B-peru gene, a promoter comprising the nucleotide sequence of SEQ ID No. 6 between positions 1 and 188, a 35S promoter, a promoter comprising the sequence of SEQ ID No. 1 between positions 447 and 1061 or a promoter comprising the sequence of SEQ ID No. 1 between positions 447 and 1061 in which TGCAG between positions 935 and 939 is changed to TTAGG.

10. The process of claim 1, in which said first genetic locus in said male-sterile parent plants and said male-fertile parent plants is a foreign genetic locus and comprises a male-sterility gene comprising a DNA encoding barnase under control of a first promoter which directs expression selectively in specific stamen cells of corn plants, and wherein said male-sterility gene is homozygous at said first genetic locus; and in which said restorer gene at said second genetic locus in said male-fertile parent plant comprises a DNA encoding barstar under control of a second promoter which directs expression at least in said specific stamen cells.

11. The process of claim 10, in which said promoter is a TA29 promoter or a CA55 promoter.

12. The process of claim 10, in which said second promoter is identical to said first promoter.

13. The process of claim 10, in which said second promoter is a TA29 promoter or a CA55 promoter.

14. The process of claim 11, in which said second promoter is identical to said first promoter.

15. The process of claim 1, in which said first genetic locus is an endogenous male-sterility locus comprising a recessive allele in homozygous condition, and in which said restorer gene is the dominant allele at said endogenous male-sterility locus.

16. A male-fertile parent plant for maintaining a male sterile corn line comprising male-sterile parent plants which comprise a homozygous male-sterility genotype at a first genetic locus, and which male-sterile parent plants do not comprise a functional regulatory gene required for anthocyanin production in corn seeds, wherein said male-fertile parent plants comprise said homozygous male-sterility genotype at said first genetic locus and further comprise, at a second genetic locus which segregates independently from said first genetic locus, foreign DNA comprising:

I) a restorer gene, the expression of which prevents the phenotypic expression of said homozygous male-sterility genotype to render said plant male-fertile; and II) at least one gene selected from the group of a first gene that is expressed in corn seeds to produce a first active regulatory protein having the same activity as the protein encoded by a functional R or B gene of corn, and a second gene that is expressed in corn seeds to produce a second active regulatory protein having the same activity as the protein encoded by a functional C1 gene of corn, wherein said foreign DNA is heterozygous at said second genetic locus, wherein said male-fertile parent plant can be crossed to said male-sterile parent plants to produce, on said male-sterile parent plants, seeds which produce anthocyanin, said anthocyanin being produced only in seeds containing said at least one gene in said foreign DNA.

17. The plant of claim 16, in which said at least one gene in said foreign DNA is expressed at least in the aleurone of corn seeds.

18. The plant of claim 17, which comprises said first gene in said foreign DNA, and which does not otherwise contain a gene that is functionally expressed in the aleurone of corn seeds which gene encodes an active regulatory protein having the same activity as the protein encoded by a functional R or B gene.

19. The plant of claim 18, in which said first gene comprises a DNA encoding a B-peru protein which is under the control of a promoter of the B-peru gene, a promoter comprising the nucleotide sequence of SEQ ID No. 6 between positions 1 and 188, a 35S promoter, a promoter comprising the sequence of SEQ ID No. 1 between positions 447 and 1061 and a promoter comprising the sequence of SEQ ID No. 1 between positions 447 and 1061 in which TGCAG between positions 935 and 939 is changed to TTAGG.

20. The plant of claim 19, in which said first gene does not comprise an intron.

21. The plant of claim 17, which comprises said second gene in said foreign DNA, and which plant does not otherwise contain a gene that is functionally expressed in the aleurone of corn seeds which gene encodes an active regulatory protein having the same activity as the protein encoded by a functional C1 gene.

22. The plant of claim 21, in which said second gene comprises a DNA encoding the C1 protein which is under control of a promoter of the B-peru gene, a promoter comprising the nucleotide sequence of SEQ ID No. 6 between positions 1 and 188, a 35S promoter, a promoter comprising the sequence of SEQ ID No. 1 between positions 447 and 1061 or a promoter comprising the sequence of SEQ ID No. 1 between positions 447 and 1061 in which TGCAG between positions 935 and 939 is changed to TTAGG.

23. The plant of claim 17, which comprises said first gene and said second gene in said foreign DNA, and which plant does not otherwise contain 1) a gene that is functionally expressed in the aleurone of corn seeds which gene encodes an active regulatory protein having the same activity as the protein encoded by a functional R or B gene, and 2) a gene that is functionally expressed in the aleurone of corn seeds which gene encodes an active regulatory protein having the same activity as the protein encoded by a functional C1 gene.

24. The plant of claim 23, in which said first gene comprises a DNA encoding the B-peru protein under the control of a promoter of the B-peru gene, a promoter comprising the nucleotide sequence of SEQ ID No. 6 between positions 1 and 188, a 35S promoter, a promoter comprising the sequence of SEQ ID No. 1 between positions 447 and 1061 or a promoter comprising the sequence of SEQ ID No. 1 between positions 447 and 1061 in which TGCAG between positions 935 and 939 is changed to TTAGG; and in which said second gene comprises a DNA encoding the C1 protein which is under the control of a promoter of the B-peru gene, a promoter comprising the nucleotide sequence of SEQ ID No. 6 between positions 1 and 188, a 35S promoter, a promoter comprising the sequence of SEQ ID No. 1 between positions 447 and 1061 and a promoter comprising the sequence of SEQ ID No. 1 between positions 447 and 1061 in which TGCAG between positions 935 and 939 is changed to TTAGG.

25. The plant of claim 16, in which said first genetic locus is a foreign genetic locus and comprises a male-sterility gene comprising a DNA encoding barnase under control of a first promoter which directs expression selectively in specific stamen cells of corn plants, and wherein said male-sterility gene is homozygous at said first genetic locus; and in which said restorer gene at said second genetic locus comprises a DNA encoding barstar under control of a second promoter which directs expression at least in said specific stamen cells.

26. The plant of claim 25, in which said first promoter is a TA29 promoter or a CA55 promoter.

27. The plant of claim 25, in which said second promoter is identical to said first promoter.

28. The plant of claim 25, in which said second promoter is a TA29 promoter or a CA55 promoter.

29. The plant of claim 26, in which said second promoter is identical of said first promoter.

30. The plant of claim 16, in which said first genetic locus is an endogenous male-sterility locus comprising a recessive allele in homozygous condition, and in which said restorer gene is the dominant allele at said endogenous male-sterility locus.

31. A kit for maintaining a male-sterile corn line, said kit comprising:
    (a) a male-sterile corn line comprising male-sterile parent plants which comprise a homozygous male-sterility genotype at a first genetic locus and which male-sterile parent plants do not comprise a regulatory gene required for anthocyanin production in corn seeds; and
    (b) a maintainer corn line comprising male-fertile parent plants which comprise said homozygous male-sterility genotype at said first genetic locus, which further comprise, at a second genetic locus which segregates independently from said first genetic locus, foreign DNA comprising:
        I) a restorer gene, whose expression prevents phenotypic expression of said homozygous male-sterility genotype; and
        II) at least one gene selected from the group of a first gene that is expressed in corn seeds to produce a first active regulatory protein having the same activity as the protein encoded by a functional R or B gene, and a second gene that is expressed in corn seeds to produce a second active regulatory protein having the same activity as the protein encoded by a functional C1 gene,
    wherein said foreign DNA is heterozygous at said second genetic locus,
    wherein said male-sterile and male-fertile parents can be crossed to produce, on said male-sterile parent plants, seeds which produce anthocyanin, said anthocyanin being produced only in seeds comprising said at least one gene in said foreign DNA.

32. The kit of claim 31, in which said at least one gene in said foreign DNA is expressed at least in the aleurone of corn seeds.

33. The kit of claim 32, in which said male-sterile parent plants do not contain a gene that is functionally expressed in the aleurone of corn seeds which gene encodes an active regulatory protein having the same activity as the protein encoded by a functional R or B gene, wherein said foreign DNA in said male-fertile parent plants comprises said first gene.

34. The kit of claim 33, in which said first gene comprises a DNA encoding the B-peru protein which is under the control of a promoter of the B-peru gene, a promoter comprising the nucleotide sequence of SEQ ID No. 6 between positions 1 and 188, a 35S promoter, a promoter comprising the sequence of SEQ ID No. 1 between positions 447 and 1061 or a promoter comprising the sequence of SEQ ID No. 1 between positions 447 and 1061 in which TGCAG between positions 935 and 939 is changed to TTAGG.

35. The kit of claim 34, in which said first gene does not comprise an intron.

36. The kit of claim 32, in which said male-sterile parent plants do not contain a gene that is functionally expressed in the aleurone of corn seeds which gene encodes an active regulatory protein having the same activity as a functional C1 gene, and wherein said foreign DNA in said male-fertile parent plants comprises said second gene.

37. The kit of claim 36, which said second gene comprises a DNA encoding the C1 protein which is under the control of a promoter of the B-peru gene, a promoter comprising the nucleotide sequence of SEQ ID No. 6 between positions 1 and 188, a 35S promoter, a promoter comprising the sequence of SEQ ID No. 1 between positions 447 and 1061 or a promoter comprising the sequence of SEQ ID No. 1 between positions 447 and 1061 in which TGCAG between positions 935 and 939 is changed to TTAGG.

38. The kit of claim 32, in which said male-sterile parent plants do not contain a gene that is functionally expressed in the aleurone of corn seeds which gene encodes an active regulatory protein having the same activity as the protein encoded by a functional R or B gene, and do not contain a gene that is functionally expressed in the aleuron of corn seeds which gene encodes an active regulatory protein having the same activity as the protein encoded by a functional C1 gene, and wherein said foreign DNA in said male-fertile parent plants contains said first gene and said second gene.

39. The kit of claim 38, in which said first gene comprises a DNA encoding the B-peru protein under the control of a promoter of the B-peru gene, a promoter comprising the nucleotide sequence of SEQ ID No. 6 between positions 1 and 188, a 35S promoter, a promoter comprising the sequence of SEQ ID No. 1 between positions 447 and 1061 or a promoter comprising the sequence of SEQ ID No. 1 between positions 447 and 1061 in which TGCAG between positions 935 and 939 is changed to TTAGG; and in which said second gene comprises a DNA encoding the C1 protein under the control of a promoter of the B-peru gene, a promoter comprising the nucleotide sequence of SEQ ID No. 6 between positions 1 and 188, a 35S promoter, a promoter comprising the sequence of SEQ ID No. 1 between positions 447 and 1061 and a promoter comprising the sequence of SEQ ID No. 1 between positions 447 and 1061 in which TGCAG between positions 935 and 939 is changed to TTAGG.

40. The kit of claim 31, in which said first genetic locus in said male-sterile plants and said male-fertile parent plants is a foreign genetic locus which comprises a male-sterility gene comprising a DNA encoding barnase under control of a first promoter which directs expression selectively in specific stamen cells of corn plants, and wherein said male-sterility gene is homozygous at said first genetic locus; and in which said restorer gene at said second genetic locus in said male-fertile parent plants comprises a DNA encoding barstar under control of a second promoter which directs expression at least in said specific stamen cells.

41. The kit of claims 40, in which said first promoter is a TA29 promoter or a CA55 promoter.

42. The kit of claim 40, in which said second promoter is identical to said first promoter.

43. The kit of the claim 40, in which said second promoter is a TA29 promoter or a CA55 promoter.

44. The kit of claim 41, in which said second promoter is identical to said first promoter.

45. The kit of claims 31, in which said first genetic locus is an endogenous male-sterility locus comprising a recessive allele in homozygous condition, and in which said restorer gene is the dominant allele at said endogenous male-sterility locus.

\* \* \* \* \*